(12) United States Patent
Jones et al.

(10) Patent No.: US 10,669,515 B2
(45) Date of Patent: Jun. 2, 2020

(54) FLUID MIXING SYSTEM WITH LATERALLY DISPLACED FLEXIBLE DRIVE LINES AND METHODS OF USE

(71) Applicant: LIFE TECHNOLOGIES CORPORATION, Carlsbad, CA (US)

(72) Inventors: Nephi D. Jones, Newton, UT (US); Christopher D. Brau, Logan, UT (US)

(73) Assignee: Life Technologies Corporation, Carlsbad, CA (US)

( * ) Notice: Subject to any disclaimer, the term of this patent is extended or adjusted under 35 U.S.C. 154(b) by 275 days.

(21) Appl. No.: 15/392,906

(22) Filed: Dec. 28, 2016

(65) Prior Publication Data

US 2017/0183617 A1    Jun. 29, 2017

Related U.S. Application Data

(60) Provisional application No. 62/272,504, filed on Dec. 29, 2015.

(51) Int. Cl.
*B01F 7/00* (2006.01)
*C12M 1/06* (2006.01)
*B01F 15/00* (2006.01)
*C12M 1/00* (2006.01)

(52) U.S. Cl.
CPC ......... *C12M 27/02* (2013.01); *B01F 7/00383* (2013.01); *B01F 7/00633* (2013.01); *B01F 7/00675* (2013.01); *B01F 15/0085* (2013.01); *B01F 15/00707* (2013.01); *C12M 23/14* (2013.01); *B01F 2215/0073* (2013.01)

(58) Field of Classification Search
CPC ........................... B01F 7/0005; B01F 7/00566
USPC .................................... 366/325.94, 326.1
See application file for complete search history.

(56) References Cited

U.S. PATENT DOCUMENTS

| | | | |
|---|---|---|---|
| 659,345 A * | 10/1900 | Ivins | A01J 9/04 165/85 |
| 1,752,833 A | 4/1930 | Brumder | |
| 1,778,188 A | 10/1930 | Guy | |
| 1,898,724 A | 2/1933 | Gifford | |
| 1,954,093 A | 4/1934 | Nelson | |

(Continued)

FOREIGN PATENT DOCUMENTS

| DE | 202009005407 U1 | 9/2009 |
|---|---|---|
| DE | 102008058338 A1 | 5/2010 |

(Continued)

OTHER PUBLICATIONS

ATMI Life Sciences, *Integrity PadReadtor, A New Culture in Cell Growth*, published as early as 2010, 4 pages.

(Continued)

*Primary Examiner* — David L Sorkin
(74) *Attorney, Agent, or Firm* — Workman Nydegger

(57) ABSTRACT

A fluid mixing system includes a container bounding a compartment and extending between a first end and an opposing second end. An elongated first drive line and second drive line are disposed within the compartment of the container and are rotatable therein. At least one tie extends between the first drive line and the second drive line so as to maintain at least a portion of the first drive line and the second drive line at lateral spaced apart positions within the compartment. An impeller or other mixing element can be coupled to the drive lines.

20 Claims, 31 Drawing Sheets

(56) References Cited

U.S. PATENT DOCUMENTS

| | | | |
|---|---|---|---|
| 3,281,124 A * | 10/1966 | Bartl | B01F 7/00558 366/325.94 |
| 3,322,401 A | 5/1967 | Mersch | |
| 3,559,962 A | 2/1971 | Enssle et al. | |
| 3,692,427 A | 9/1972 | Risse | |
| 4,083,653 A | 4/1978 | Stiffler | |
| 4,722,608 A | 2/1988 | Salzman et al. | |
| 5,885,001 A | 3/1999 | Thomas | |
| 5,941,636 A | 8/1999 | Lu | |
| 6,083,587 A | 7/2000 | Smith et al. | |
| 6,670,171 B2 | 12/2003 | Carll | |
| 6,844,186 B2 | 1/2005 | Carll | |
| 7,384,783 B2 | 6/2008 | Kunas et al. | |
| 7,441,940 B2 | 10/2008 | Vanek | |
| 7,487,688 B2 | 2/2009 | Goodwin | |
| 7,682,067 B2 | 3/2010 | West et al. | |
| 7,878,099 B2 | 2/2011 | Loibl | |
| 7,879,599 B2 | 2/2011 | Goodwin et al. | |
| 8,342,737 B2 | 1/2013 | Greller et al. | |
| 8,455,242 B2 | 6/2013 | Staheli et al. | |
| 8,506,198 B2 | 8/2013 | West et al. | |
| 8,603,805 B2 | 12/2013 | Goodwin et al. | |
| 8,641,314 B2 | 2/2014 | Thacker et al. | |
| 9,839,886 B2 | 12/2017 | Staheli | |
| 2002/0105856 A1 | 8/2002 | Terentiev | |
| 2002/0131654 A1 | 9/2002 | Smith et al. | |
| 2003/0077466 A1 | 4/2003 | Smith et al. | |
| 2006/0240546 A1 | 10/2006 | Goodwin et al. | |
| 2006/0270036 A1 | 11/2006 | Goodwin et al. | |
| 2007/0014187 A1 * | 1/2007 | Kaas | A21C 1/02 366/325.6 |
| 2010/0165785 A1 * | 7/2010 | Kaas | A21C 1/02 366/325.6 |
| 2010/0260010 A1 | 10/2010 | Jornitz | |
| 2011/0013473 A1 | 1/2011 | Ludwig et al. | |
| 2011/0013474 A1 | 1/2011 | Ludwig et al. | |
| 2011/0026360 A1 | 2/2011 | Greller et al. | |
| 2011/0058447 A1 | 3/2011 | Reif et al. | |
| 2011/0058448 A1 | 3/2011 | Reif et al. | |
| 2011/0188928 A1 | 8/2011 | West et al. | |
| 2011/0229963 A1 | 9/2011 | Fatherazi et al. | |
| 2011/0310696 A1 | 12/2011 | Goodwin et al. | |
| 2013/0101982 A1 | 4/2013 | Goodwin et al. | |
| 2014/0106453 A1 | 4/2014 | Kunas et al. | |
| 2015/0117142 A1 | 4/2015 | Staheli et al. | |

FOREIGN PATENT DOCUMENTS

| | | |
|---|---|---|
| FR | 782935 | 9/1934 |
| JP | H06285353 A | 10/1994 |
| WO | 2011/139209 A1 | 11/2011 |
| WO | 2013/151733 A1 | 10/2013 |

OTHER PUBLICATIONS

ATMI Life Sciences, *Integrity PadReadtor, All Applications, High-End Controls and Abilities*, published as early as 2010, 4 pages.

International Search Report and Written Opinion dated Apr. 20, 2017, issued in PCT Application No. PCT/US2016/068064, filed Dec. 21, 2016.

* cited by examiner

FLUID MIXING SYSTEM WITH LATERALLY DISPLACED FLEXIBLE DRIVE LINES AND METHODS OF USE

CROSS-REFERENCE TO RELATED APPLICATIONS

This application claims priority to U.S. Provisional Application No. 62/272,504, filed Dec. 29, 2015, which is incorporated herein by specific reference.

BACKGROUND OF THE INVENTION

1. The Field of the Invention

The present invention relates to fluid mixing systems and, more specifically, fluid mixing systems having at least two laterally displaced flexible drive lines.

2. The Relevant Technology

The biopharmaceutical industry uses a broad range of mixing systems for a variety of processes such as in the preparation of media and buffers and in the growing, mixing and suspension of cells and microorganisms. Some conventional mixing systems, including bioreactors and fermentors, comprise a flexible bag disposed within a rigid support housing. An impeller is disposed within the flexible bag and is coupled with the drive shaft. Rotation of the drive shaft and impeller facilitates mixing and/or suspension of the fluid contained within flexible bag.

Although the current mixing systems are useful, they have some limitations. For example, where the drive shaft is secured within the flexible bag during the manufacturing process, the rigid drive shaft limits the ability to collapse or fold the flexible bag so as to reduce its size for transportation, storage and/or further processing. Likewise, where it is intended to reuse the drive shaft, such as when it is made of metal, this system has the disadvantage of needing to clean and sterilize the drive shaft between different uses.

In an alternative conventional system, a rotatable tube extends into the flexible bag and has an impeller coupled at the end thereof. During use, the rigid drive shaft is passed down into the tube and couples with the impeller. In turn, rotation of the drive shaft facilitates rotation of the impeller for mixing the fluid within the flexible bag. In this design, with the drive shaft removed, the flexible bag with tube can be folded for ease of storage and transportation. In addition, because the drive shaft does not directly contact the fluid within the bag, the drive shaft does not need to be cleaned or sterilized between uses.

However, the flexible bag is typically secured within the support housing prior to insertion of the drive shaft. It is thus necessary during use to vertically position the drive shaft over the top of the bag for insertion into the tube. For large bags or elongated bags that require a long drive shaft, this can be difficult to accomplish. Furthermore, in situations where the mixing system is located in a room with a relatively low ceiling, it may be impossible to vertically lift the drive shaft over the bag. This type of system also requires increased training in user operation to ensure that the drive shaft is properly received within the tube and properly engaged with the impeller so that the system operates as intended.

In one attempt to alleviate some of the above problems, International Publication No. WO 2013/151733 A1 discloses a fluid mixing system that comprises a flexible bag having a single flexible drive line that is rotatably disposed within the bag and extends to opposing ends of the bag. An impeller is mounted on the flexible drive line. Rotation of the drive line from outside of the bag rotates the impeller which mixes fluid within the bag. Because the drive line is flexible, the bag can be folded with the drive line therein for compact storage and transport. Furthermore, the flexible drive line eliminates the need for an elongated drive shaft to be inserted into the bag. As such, the system eliminates the need for a long drive shaft and can be easily used in facilities having a low ceiling. However, as discussed below in more detail, the system using the single flexible drive line has its own shortcomings. Accordingly, what is needed in the art are mixing systems that solve all or some of the above problems.

SUMMARY OF THE INVENTION

According to a first independent aspect of the present invention a fluid mixing system is provided, the fluid mixing system comprising:
  a container bounding a compartment, the container having a first end and an opposing second end;
  an elongated first drive line disposed within the compartment of the container and having a length extending between a first end and an opposing second end, at least a portion of the length of the first drive line being flexible;
  an elongated second drive line disposed within the compartment of the container and having a length extending between a first end and an opposing second end, at least a portion of the length of the second drive line being flexible, the first drive line and second drive line being rotatable within the compartment of the container; and
  at least one tie extending between the first drive line and the second drive line so as to maintain at least a portion of the first drive line and the second drive line at lateral spaced apart positions within the compartment.

The at least one tie may comprise a plurality of spaced apart ties extending between the first drive line and the second drive line and being spaced apart along the length of the first drive line and the second drive line, the plurality of ties maintaining the at least a portion of the first drive line and the second drive line at lateral spaced apart positions.

The plurality of spaced apart ties may comprise at least 3 or preferably at least 5, at least 7 or at least 9 spaced apart ties.

At least portions of the first drive line and the second drive line may be laterally spaced apart and disposed in parallel alignment.

The at least one tie may comprise a first tie that projects normal from the first drive line. The first tie may also project normal from the second drive line.

The at least one tie may comprise a first tie that connects to the first drive line and the second drive line at a plurality of spaced apart locations along the length of the first drive line and the second drive line.

The at least one tie may comprise a first tie that projects at an acute angle from the first drive line.

At least 30%, and preferably at least 50%, at least 70% or at least 90% of the length of the first drive line and the second drive line can be maintained at lateral spaced apart positions within the compartment of the container when the first drive line and second drive line are stationary and/or when the first drive line and second drive line are rotated within the compartment of the container.

The first drive line and the second drive line may be connected together at their first ends and/or at their second ends.

The first drive line and/or the second drive line may extend between the first end and the second end of the container.

The at least one tie may be more rigid than the first drive line and the second drive line.

The entire length of the first drive line and the second drive line may be flexible.

The first drive line and the second drive line may each have a longitudinal axis extending along the length thereof. At least 40%, at least 60%, or at least 80% of the length of the first drive line and/or the second drive line may be sufficient flexible that it can be twisted under torsion about its longitudinal axis over the angle of at least 180°, at least 360°, or at least 720° without plastic deformation.

The first drive line and the second drive line may each have a longitudinal axis extending along the length thereof. At least 40%, at least 60%, or at least 80% of the length of the first drive line and/or the second drive line may be sufficiently flexible that it can be bent along the longitudinal axis at an angle of at least 45°, at least 90°, at least 180°, at least 270°, or at least 360° without plastic deformation of the drive line.

The at least a portion of the length of the first drive line and/or the second drive line may have a bend radius wrapped 180° in a range between about 2 cm to about 100 cm without plastic deformation.

The first drive line and/or the second drive line may comprise a flexible cable, cord, tube, or solid line.

The first drive line and/or the second drive line may comprise a plurality of polymeric strands woven together.

The first drive line and/or the second drive line may be comprised of a ultra-high molecular weight polyethylene (UHMwPE).

The first drive line and/or the second drive line may have a maximum or a minimum diameter that can be greater than, less than, or equal to 2 mm, 4 mm, 6 mm, 8 mm, 10 mm, 15 mm, or 20 mm or in a range between any two of the foregoing.

The at least a portion of the first drive line and the second drive line may be lateral spaced apart by a distance of at least 2 cm, at least 4 cm, at least 6 cm, at least 9 cm, at least 12, or at least 15 cm.

An elongated third drive line may be disposed within the compartment of the container and have a length extending between a first end and an opposing second end.

The at least one tie may extend between the second drive line and the third drive line so as to maintain at least a portion of the first drive line, the second drive line, and the third drive line at lateral spaced apart positions within the compartment of the container.

An elongated fourth drive line may be disposed within the compartment of the container and have a length extending between a first end and an opposing second end.

The at least one tie may extend between the third drive line and the fourth drive line so as to maintain at least a portion of the first drive line, the second drive line, the third drive line and the fourth drive line at lateral spaced apart positions within the compartment of the container.

The third drive line and/or the fourth drive line or portions thereof can have the same flexible properties as the first drive line and/or the second drive line or portions thereof as set forth above or set out elsewhere in this document.

At least one mixing element may be secured to the at least one tie. At least one mixing element may be secured to the first drive line and/or second drive line.

The at least on mixing element may comprise a plurality of mixing elements secured to the first drive line and second drive line at spaced apart locations along the length of the first drive line and the second drive line.

The at least on mixing element may comprise an impeller.

The container may be rigid and the compartment thereof configured to hold a fluid.

The container may comprise a collapsible bag. The collapsible bag may be formed from one or more sheets of polymeric film.

The polymeric film may have a thickness that is less than 0.02 mm, 0.05 mm, 0.1 mm, 0.2 mm, 0.5 mm, 1 mm, 2 mm, 3 mm or in a range between any two of the foregoing.

The film is may be sufficiently flexible that it can be rolled into a tube without plastic deformation and/or can be folded over an angle of at least 90°, 180°, 270°, or 360° without plastic deformation.

The film may be a laminated and extruded film. The laminated or extruded film may have a number of layers that is at least or less than 1, 3, 5, 7, or 9 layers or in a range between any two of the foregoing. The extruded film may be a cast film such as a multi-layer co-extruded cast film.

The compartment of the collapsible bag may be sterile.

The first end of the first drive line and the second drive line may be rotatably connected to the first end of the container. The second end of the first drive line and the second drive line may be rotatably connected to the second end of the container.

A support housing may have a chamber in which the container is at least partially disposed.

Means may be provided for holding the second end of the container stationary while the first and second drive lines are rotated within the compartment of the container.

The means for holding the second end of the container stationary may comprise a retainer mounted to or disposed below the support housing and secured to the second end of the container.

Means may be provided for rotating the first drive line and the second drive line. In one sub-aspect of the invention, the means for rotating may comprise a rigid drive shaft coupled to the first end of the first drive line and the second drive line and a drive motor assembly coupled with the drive shaft.

A further sub-aspect of the invention may include:
a first rotational assembly that comprises:
  a first casing mounted to the first end of the container; and
  a first hub rotatably mounted to the first casing, the first hub being coupled to the first end of the first drive line and the second drive line; and
a second rotational assembly, the second rotational assembly including:
  a second casing mounted to the second end of the container; and
  a second hub rotatably mounted to the second casing, the second hub being coupled to the second end of the first drive line and the second drive line.

The retainer may be coupled with the second hub.

A rigid drive shaft may be coupled to the first hub.

A further sub-aspect of the present invention can comprise:
  the container having a side wall extending between the first end and the second end of the container;
  the first end of the first drive line and the second drive line being rotatably coupled to the first end of the container;

the second end of the first drive line and the second drive line being coupled to a hub; and a lateral support assembly projecting from the sidewall of the container, the hub being rotatably coupled to the lateral support assembly.

The lateral support assembly may comprise:

a retention assembly having a first end coupled to the side wall of the container, a second end secured to the hub so that the hub can freely rotate, and a tube extending between the first end and the second end; and a support rod removably received within the tube of the retention assembly.

The retention assembly may comprise an inner housing secured to the hub, an outer housing secured to the tube, and a bearing disposed between the inner housing and the outer housing.

A further sub-aspect of the present invention may comprise:

a support housing having a sidewall and bounding a chamber in which the container is at least partially disposed; and a locking fitting disposed on the sidewall of the support housing, the locking fitting having a passage extending therethrough so as to communicate with the chamber of the support housing, the support rod passing through the passage of the locking fitting.

The retention assembly may comprise a port fitting disposed at the first end thereof and coupled with the tube, the port fitting being removably coupled to the locking fitting.

A further sub-aspect of the present invention may comprise:

the container having a side wall extending between the first end and the second end of the container;

the first end of the first drive line and the second drive line being rotatably coupled to the first end of the container; and at least one guy-line projecting from the container, the second end of the first drive line and the second drive line being rotatably coupled to the at least one guy-line.

The first drive line, the second drive line, and the at least one tie may be concurrently rotatable with in the compartment of the container.

The first drive line and the second drive line may be concurrently rotatable about a common axis of rotation.

In one sub-aspect of the present invention means may be provided for rotating the first drive line and the second drive line within the compartment of the container.

The means for rotating the first drive line and the second drive line may comprise:

a drive shaft removably coupled with the first ends or the second ends of the first and second drive lines; and a drive motor assembly that selectively rotates the drive shaft.

According to a second independent aspect of the present invention, a method for mixing a fluid may comprise:

inserting a container assembly into a chamber of a support housing, the container assembly comprising:

a flexible bag bounding a compartment and a first drive line and a second drive line disposed within compartment so that the drive lines are laterally spaced apart; and rotating the first and second drive lines within the container so as to cause the drive lines to twist into a helical configuration.

One end of the flexible bag may be secured relative to the support housing prior to rotating the first and second drive lines.

The step of securing may comprise securing one end of the flexible bag to a floor of the support housing prior to rotating the first and second drive lines.

A biological culture comprised of cells or microorganisms may be dispensed into the compartment of the flexible bag. The first and second drive lines may be rotated causing mixing of the biological culture.

A first end of the first drive line and the second drive line may be secured to a hub that is rotatably coupled to the flexible bag. A drive shaft may be coupled to the hub. The drive shaft to facilitate rotation of the hub and the first and second drive lines.

The second aspect of the invention may include any of the features, options and possibilities set out elsewhere in this document, including in the first aspect and other aspects of the invention.

According to a third independent aspect of the present invention, a method for mixing a fluid comprises:

dispensing a fluid into the compartment of a container, a flexible first drive line and a flexible second drive line being disposed within compartment so that the drive lines are laterally spaced apart; and rotating the first and second drive lines within the container so as to cause the drive lines to twist into a helical configuration.

The third aspect of the invention may include any of the features, options and possibilities set out elsewhere in this document, including in the above first and second aspect of the invention.

BRIEF DESCRIPTION OF THE DRAWINGS

Various embodiments of the present invention will now be discussed with reference to the appended drawings. It is appreciated that these drawings depict only typical embodiments of the invention and are therefore not to be considered limiting of its scope.

DETAILED DESCRIPTION OF THE PREFERRED EMBODIMENTS

Figure 1:
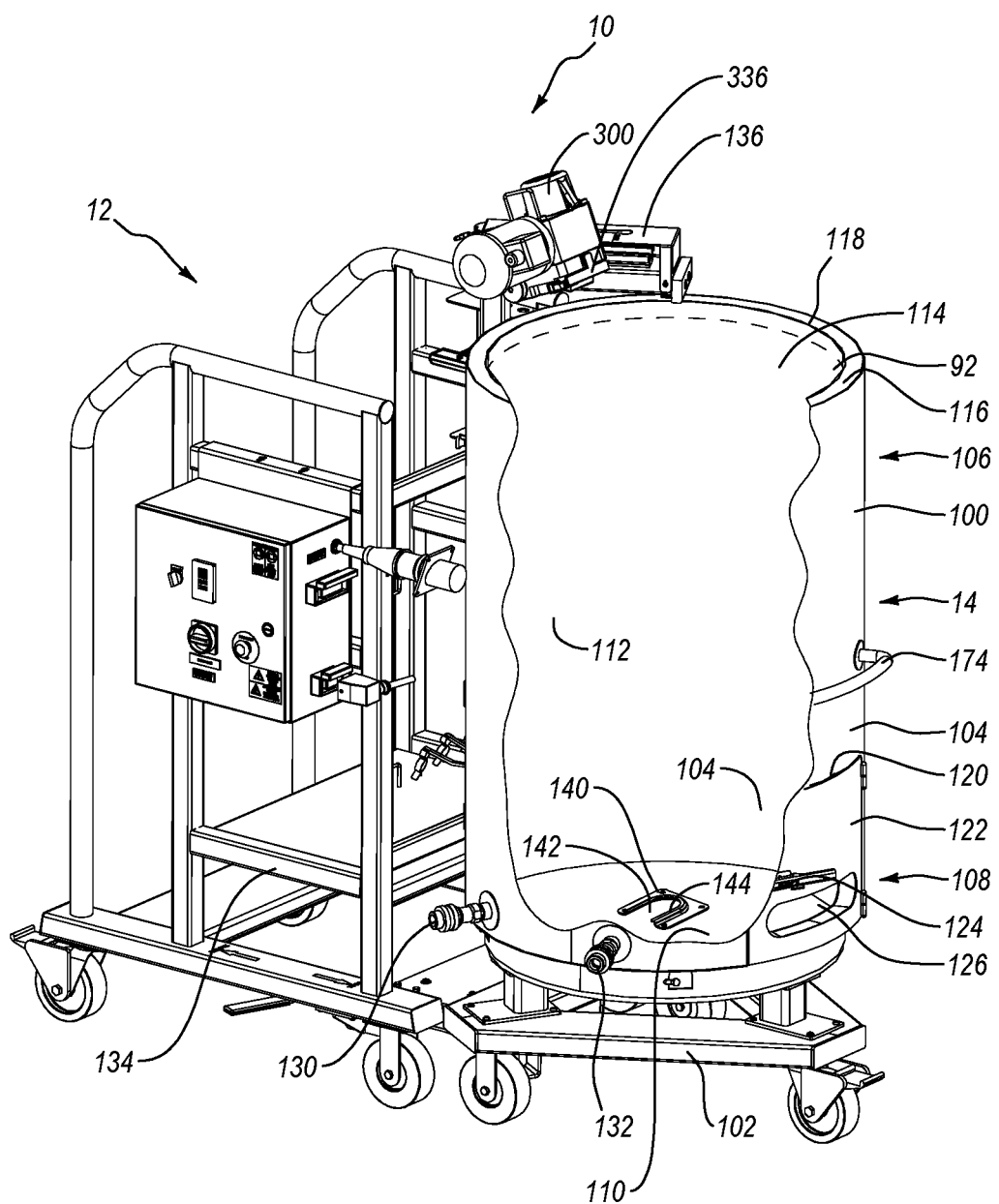
FIG. 1 is a perspective view of a support housing and docking station forming part of a fluid mixing system.

Before describing various embodiments of the present disclosure in detail, it is to be understood that this disclosure is not limited to the parameters of the particularly exemplified systems, methods, and/or products, which may, of course, vary. Thus, while certain embodiments of the present disclosure will be described in detail, with reference to specific configurations, parameters, features (e.g., components, members, elements, parts, and/or portions), etc., the descriptions are illustrative and are not to be construed as limiting the scope of the claimed invention. In addition, the terminology used herein is for the purpose of describing the embodiments, and is not necessarily intended to limit the scope of the claimed invention.

Unless defined otherwise, all technical and scientific terms used herein have the same meaning as commonly understood by one of ordinary skill in the art to which the present disclosure pertains.

Various aspects of the present disclosure, including systems, processes, and/or products may be illustrated with reference to one or more embodiments or implementations, which are exemplary in nature. As used herein, the terms "embodiment" and implementation" mean "serving as an example, instance, or illustration," and should not necessarily be construed as preferred or advantageous over other aspects disclosed herein. In addition, reference to an "implementation" of the present disclosure or invention includes a specific reference to one or more embodiments thereof, and vice versa, and is intended to provide illustrative examples without limiting the scope of the invention, which is indicated by the appended claims rather than by the following description.

As used throughout this application the words "can" and "may" are used in a permissive sense (i.e., meaning having the potential to), rather than the mandatory sense (i.e., meaning must). Additionally, the terms "including," "having," "involving," "containing," "characterized by," as well as variants thereof (e.g., "includes," "has," and "involves," "contains," etc.), and similar terms as used herein, including the claims, shall be inclusive and/or open-ended, shall have the same meaning as the word "comprising" and variants thereof (e.g., "comprise" and "comprises"), and do not exclude additional, un-recited elements or method steps, illustratively.

It will be noted that, as used in this specification and the appended claims, the singular forms "a," "an" and "the" include plural referents unless the context clearly dictates otherwise. Thus, for example, reference to a "bristle" includes one, two, or more bristles.

As used herein, directional terms, such as "top," "bottom," "left," "right," "up," "down," "upper," "lower," "proximal," "distal" and the like are used herein solely to indicate relative directions and are not otherwise intended to limit the scope of the disclosure and/or claimed invention.

Various aspects of the present disclosure can be illustrated by describing components that are bound, coupled, attached, connected, and/or joined together. As used herein, the terms "bound," "coupled", "attached", "connected," and/or "joined" are used to indicate either a direct association between two components or, where appropriate, an indirect association with one another through intervening or intermediate components. In contrast, when a component is referred to as being "directly bound," "directly coupled", "directly attached", "directly connected," and/or "directly joined" to another component, no intervening elements are present or contemplated. Furthermore, binding, coupling, attaching, connecting, and/or joining can comprise mechanical and/or chemical association.

To facilitate understanding, like reference numerals (i.e., like numbering of components and/or elements) have been used, where possible, to designate like elements common to the figures. Specifically, in the exemplary embodiments illustrated in the figures, like structures, or structures with like functions, will be provided with similar reference designations, where possible. Specific language will be used herein to describe the exemplary embodiments. Nevertheless, it will be understood that no limitation of the scope of the disclosure is thereby intended. Rather, it is to be understood that the language used to describe the exemplary embodiments is illustrative only and is not to be construed as limiting the scope of the disclosure (unless such language is expressly described herein as essential). Furthermore, multiple instances of an element and or sub-elements of a parent element may each include separate letters appended to the element number. Furthermore, an element label with an appended letter can be used to designate an alternative design, structure, function, implementation, and/or embodiment of an element or feature without an appended letter. Likewise, an element label with an appended letter can be used to indicate a sub-element of a parent element. However, element labels including an appended letter are not meant to be limited to the specific and/or particular embodiment(s) in which they are illustrated. In other words, reference to a specific feature in relation to one embodiment should not be construed as being limited to applications only within said embodiment.

It will also be appreciated that where multiple possibilities of values or a range a values (e.g., less than, greater than, at least, or up to a certain value, or between two recited values) is disclosed or recited, any specific value or range of values falling within the disclosed range of values is likewise disclosed and contemplated herein. Thus, disclosure of an illustrative measurement or distance less than or equal to about 10 units or between 0 and 10 units includes, illustratively, a specific disclosure of: (i) a measurement of 9 units, 5 units, 1 units, or any other value between 0 and 10 units, including 0 units and/or 10 units; and/or (ii) a measurement between 9 units and 1 unit, between 8 units and 2 units, between 6 units and 4 units, and/or any other range of values between 0 and 10 units.

The headings used herein are for organizational purposes only and are not meant to be used to limit the scope of the description or the claims.

The present invention relates to systems and methods for mixing fluid. The mixed fluid can comprise a solution, suspension, colloid, emulsion, or other mixture. The systems can commonly be used as bioreactors or fermentors for culturing cells or microorganisms. By way of example and not by limitation, the inventive systems can be used in culturing bacteria, fungi, algae, plant cells, animal cells, protozoan, nematodes, and the like. The systems can accommodate cells and microorganisms that are aerobic or anaerobic and are adherent or non-adherent. The systems can also be used in association with the formation and/or processing of fluid mixtures that are for biological purposes, such as media, buffers, or reagents. The systems can further be used for mixing powders or other components into a liquid and for preparing or processing fluid mixtures that are for non-biological purposes such as in the formation and/or processing of chemicals, medications, beverages, food products, food additives, and other products.

Reference will now be made the figures of the present disclosure. It is noted that the figures are not necessarily drawn to scale and that the size, orientation, position, and/or relationship of or between various components can be altered in some embodiments without departing from the scope of this disclosure.

Figure 2:
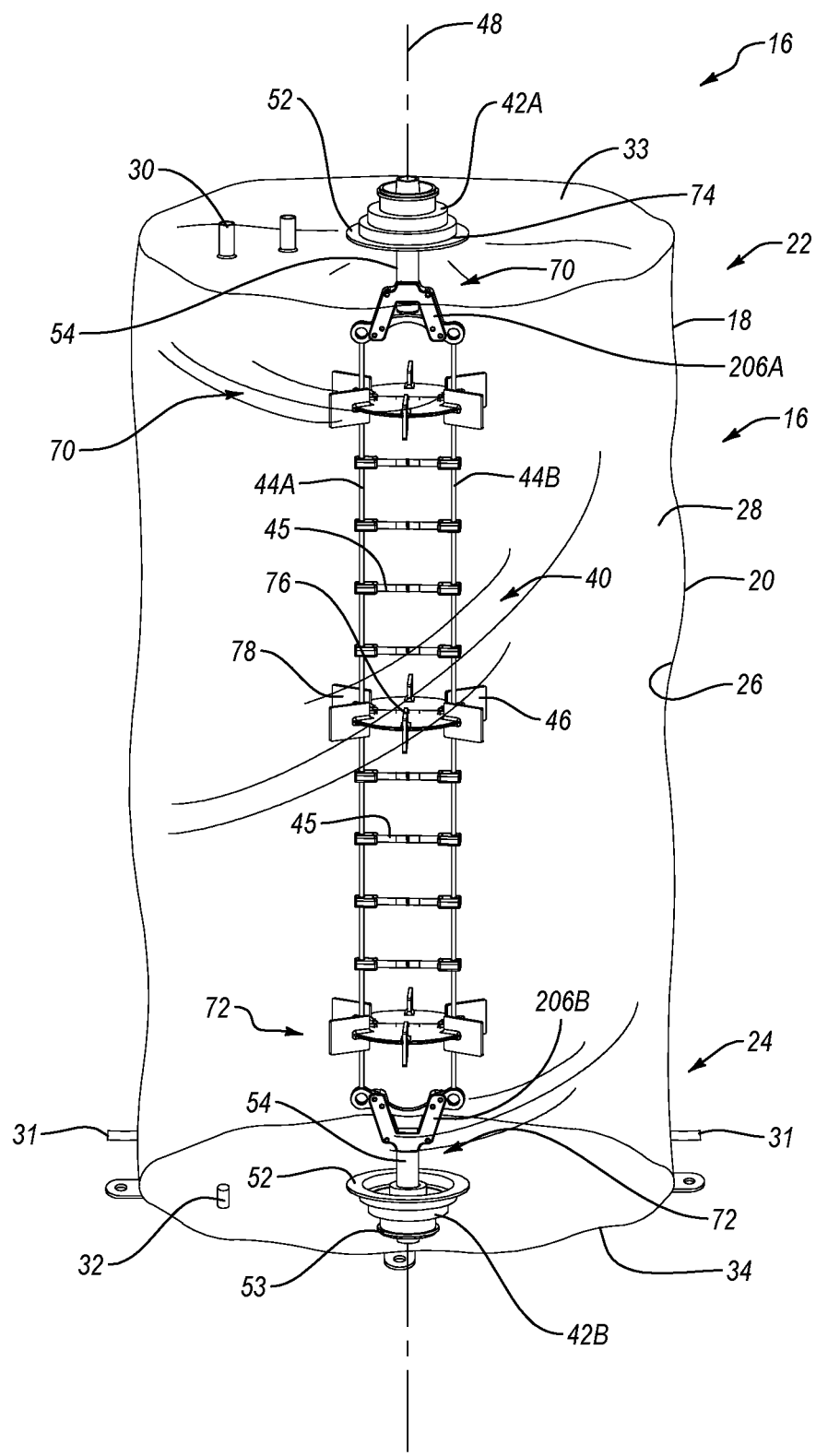
FIG. 2 is a perspective view of a container assembly for use with a support housing shown in FIG. 1.
Figure 3:
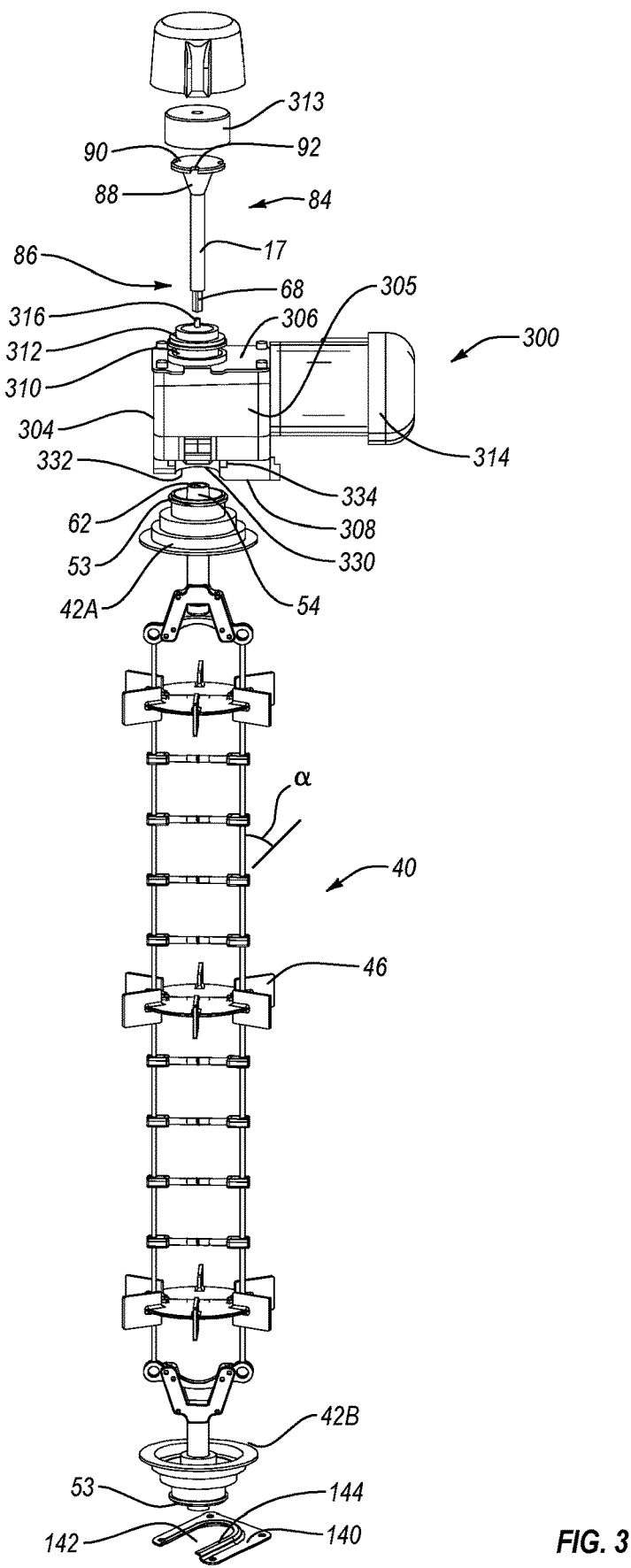
FIG. 3 is a partially exploded view of the mixing assembly, drive motor assembly, and drive shaft of the fluid mixing system.

Depicted in FIGS. 1-3 is one embodiment of an inventive fluid mixing system 10 incorporating features of the present invention. In general, mixing system 10 comprises a docking station 12, a container station 14 that removably docks with docking station 12, a container assembly 16 (FIG. 2) that is supported by container station 14, and a drive shaft 17 (FIG. 3) that extends between docking station 12 and container assembly 16. Container assembly 16 houses the fluid that is mixed. The various components of fluid mixing system 10 will now be discussed in greater detail.

As depicted in FIG. 2, container assembly 16 comprises a container 18 having a side 20 that extends from an upper end 22 to an opposing lower end 24. Upper end 22 terminates at an upper end wall 33 while lower end 24 terminates at a lower end wall 34. Container 18 also has an interior surface 26 that bounds a compartment 28. Compartment 28 is configured to hold a fluid. In the embodiment depicted, container 18 comprises a flexible and collapsible bag that is comprised of a flexible, water impermeable material such as a low-density polyethylene or other polymeric sheets of film having a thickness in a range between about 0.1 mm to about 5 mm with about 0.2 mm to about 2 mm being more common. The polymeric film can have a thickness that is at least or less than 0.02 mm, 0.05 mm, 0.1 mm, 0.2 mm, 0.5 mm, 1 mm, 2 mm, 3 mm or in a range between any two of the foregoing. Other thicknesses can also be used. The film is typically sufficiently flexible that it can be rolled into a tube without plastic deformation and/or can be folded over an angle of at least 90°, 180°, 270°, or 360° without plastic deformation.

The material can be comprised of a single ply material or can comprise two or more layers which are either sealed together or separated to form a double wall container. Where the layers are sealed together, the material can comprise a laminated or extruded material. The laminated material comprises two or more separately formed layers that are subsequently secured together by an adhesive. The laminated and extruded films typically have between 1-9 layers and more commonly between 3-9 layers. The films used can commonly have a number of layers that is at least or less than 1, 3, 5, 7, or 9 layers or in a range between any two of the foregoing. The extruded film can be a cast film such as a multi-layer co-extruded cast film. Examples of extruded material that can be used in the present invention include the Thermo Scientific CX3-9 and Thermo Scientific CX5-14 films available from Thermo Fisher Scientific. The material can be approved for direct contact with living cells and be capable of maintaining a solution sterile. In such an embodiment, the material can also be sterilizable such as by ionizing radiation.

In one embodiment, container 18 can comprise a two-dimensional pillow style bag. In another embodiment, container 18 can be formed from a continuous tubular extrusion of polymeric material that is cut to length. The ends can be seamed closed or panels can be sealed over the open ends to form a three-dimensional bag. Three-dimensional bags not only have an annular side wall but also a two dimensional top end wall and a two dimensional bottom end wall. Three dimensional containers can comprise a plurality of discrete panels, typically three or more, and more commonly four or six. Each panel is substantially identical and comprises a portion of the side wall, top end wall, and bottom end wall of the container. Corresponding perimeter edges of each panel are seamed together. The seams are typically formed using methods known in the art such as heat energies, RF energies, sonics, or other sealing energies.

In alternative embodiments, the panels can be formed in a variety of different patterns. Further disclosure with regard to one method of manufacturing three-dimensional bags is disclosed in United States Patent Publication No. US 2002-

0131654 A1, published Sep. 19, 2002 which is incorporated herein by specific reference in its entirety.

It is appreciated that container 18 can be manufactured to have virtually any desired size, shape, and configuration. For example, container 18 can be formed having compartment 28 sized to be greater than, smaller than or equal to 10 liters, 30 liters, 100 liters, 250 liters, 500 liters, 750 liters, 1,000 liters, 1,500 liters, 3,000 liters, 5,000 liters, 10,000 liters or other desired volumes. The size of compartment 28 can also be in the range between any two of the above volumes. Although container 18 can be any shape, in one embodiment container 18 is specifically configured to be generally complementary to the chamber on container station 14 in which container 18 is received so that container 18 is properly supported within the chamber.

Although in the above discussed embodiment container 18 is depicted as a flexible bag, in alternative embodiments it is appreciated that container 18 can comprise other forms of collapsible containers or semi-rigid containers. Container 18 can also be transparent or opaque.

Continuing with FIG. 2, formed on container 18 are a plurality of ports 30 at upper end 22, a plurality of ports 31 on opposing sides of side 20 at lower end 24 and a port 32 on lower end wall 34. Each of ports 30-32 communicate with compartment 28. Although only a few ports 30-32 are shown, it is appreciated that container 18 can be formed with any desired number of ports 30-32 and that ports 30-32 can be formed at any desired location on container 18. Ports 30-32 can be the same configuration or different configurations and can be used for a variety of different purposes. For example, ports 30 can be coupled with fluid lines for delivering media, cell cultures, and/or other components into container 18 and withdrawing fluid from container 18. Ports 30 can also be used for delivering gas to container 18, such as through a sparger, and withdrawing gas from container 18.

Ports 30-32 can also be used for coupling probes and/or sensors to container 18. For example, when container 18 is used as a bioreactor or fermentor for growing cells or microorganisms, ports 30-32 can be used for coupling probes such as temperatures probes, pH probes, dissolved oxygen probes, and the like. Various optical sensors and other types of sensors can also be attached to ports 30-32. Examples of ports 30-32 and how various probes, sensors, and lines can be coupled thereto is disclosed in United States Patent Publication No. 2006-0270036, published Nov. 30, 2006 and United States Patent Publication No. 2006-0240546, published Oct. 26, 2006, which are incorporated herein by specific reference in their entirety. Ports 30-32 can also be used for coupling container 18 to secondary containers, to condenser systems, and to other desired fittings.

Container assembly 16 further comprises a mixing assembly 40. In general, mixing assembly 40 comprises a first rotational assembly 42A mounted on upper end wall 33, a second rotational assembly 42B mounted on lower end wall 34, elongated and flexible first and second drive lines 44A and 44B that extend between rotational assemblies 42A and 42B. A plurality of ties 45 extend between drive lines 44A and 44B at spaced apart locations along the length of drive lines 44A and 44B.

Figure 4:
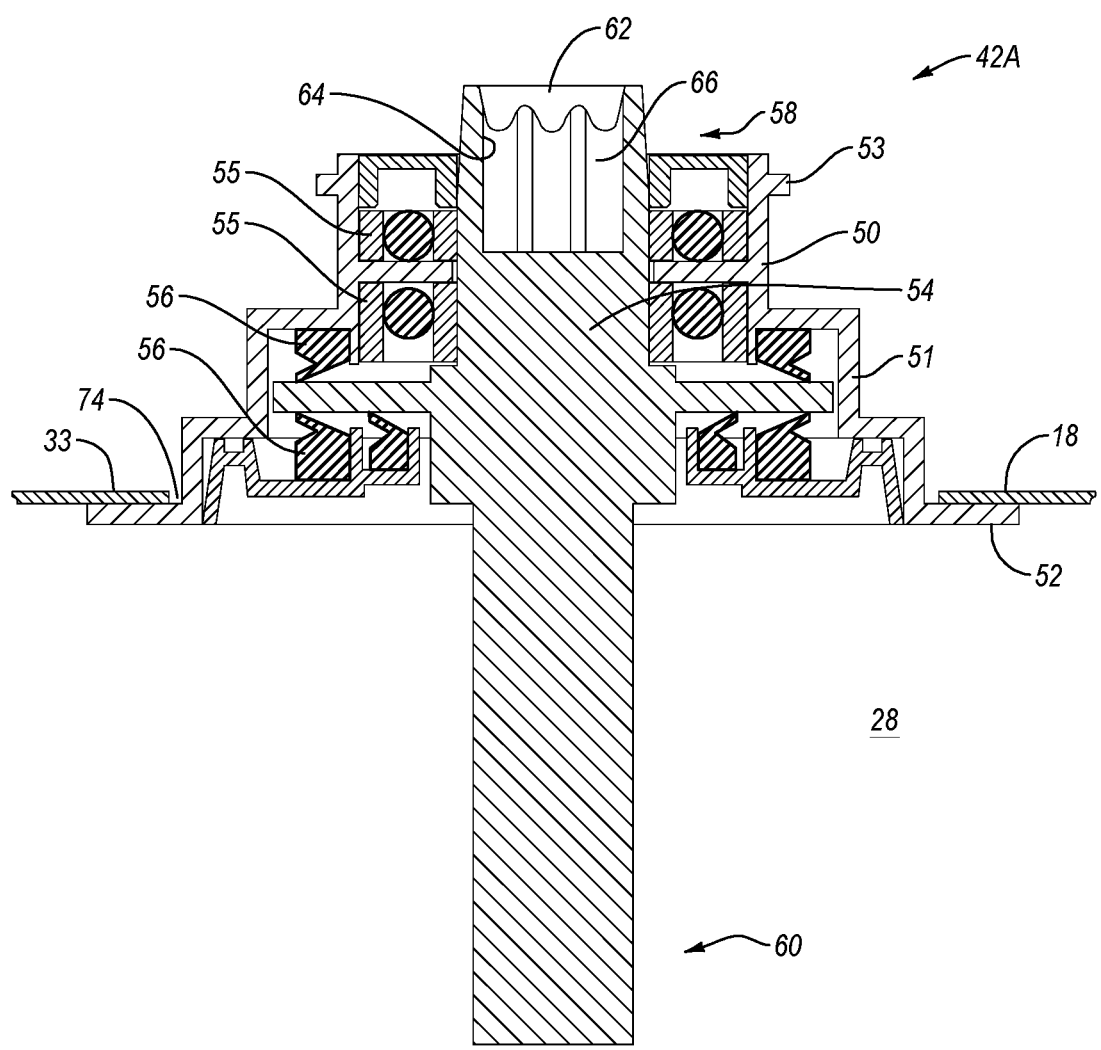
FIG. 4 is a cross sectional side view of the first rotational assembly shown in FIG. 3.

As depicted in FIG. 4, rotational assembly 42A comprises an outer casing 50 that includes an annular body 51 having a passage that extends therethrough, an annular sealing flange 52 that outwardly projects from a first end of body 51 and an annular mounting flange 53 that outwardly projects from a second end of body 51. A hub 54 is rotatably disposed within outer casing 50. One or more bearing assemblies 55 can be disposed between outer casing 50 and hub 54 to permit free and easy rotation of hub 54 relative to casing 50. Likewise, one or more seals 56 can be disposed between outer casing 50 and hub 54 so that during use an aseptic seal can be maintained between outer casing 50 and hub 54 as hub 54 rotates relative to outer casing 50. Hub 54 has a first end 58 that is disposed outside of container 18 and an opposing second end 60 that is disposed within container 18. An engaging portion is formed on first end 58 and is configured to engage with drive shaft 17 (FIG. 3). In the depicted embodiment, the engaging portion is depicted as an opening 66, such as in the form of a recessed socket, having a polygonal or other non-circular transverse cross section that is configured to mate to an end of drive shaft 17 so that rotation of drive shaft 17 facilitates rotation of hub 54. Other engagements between drive shaft 17 and hub 54 can also be used.

Rotational assembly 42A is secured to container 18. Specifically, in the depicted embodiment container 18 has an opening 74 extending through upper end wall 33. Sealing flange 52 of outer casing 50 is sealed, such as by welding or adhesive, around the perimeter bounding opening 74 so that hub 54 communicates with compartment 28. Flange 52 can be welded on the interior or exterior surface of container 18. In this configuration, outer casing 50 is fixed to container 18 but hub 54, and thus also drive lines 44, can freely rotate relative to outer casing 50 and container 18. As a result of rotational assembly 42A sealing opening 74, compartment 28 is sealed closed so that container 18 can be used in processing sterile fluids.

Turning to FIG. 2, rotational assembly 42B can have the same configuration as rotational assembly 42A and can be mounted to lower end wall 34 of container 18 in the same manner that rotational assembly 42A is mounted to container 18. Like elements between rotational assemblies 42A and 42B are identified by like reference characters. As noted above and discussed below in greater detail, drive shaft 17 (FIG. 3) is used to engage and rotate hub 54 of rotational assembly 42A. In the above configuration, a separate drive shaft could also be used to engage and rotate hub 54 of rotational assembly 42B. In other embodiments, hub 54 of rotational assembly 42A need not be engaged and rotated by drive shaft 17 but rather hub 54 of rotational assembly 42B can be solely rotated by a dive shaft extending up from the bottom of container assembly 16 to facilitate rotation of drive lines 44. Likewise, hub 54 of rotational assembly 42B need not be directly engaged and rotated by a separate drive shaft and thus opening 66 (FIG. 4) on hub 54 of rotational assembly 42B can be eliminated.

Each drive line 44 is elongated and extends from a first end 70 to an opposing second end 72. Drive lines 44 can be made from a variety of different flexible materials and can have different configurations. By way of example and not be limitation, in one embodiment drive lines 44 can be made from a braded or woven material such as cable, cord or rope. The braded material can be made from a plurality of different strands that are comprised of metal, polymer, composite or other materials that have desired strength and flexibility properties and can be sterilized. For example, the strands can be made from metal like stainless steel or a polymer like ultra-high molecular weight polyethylene (UHMwPE) such as that sold under the trademark DYNEEMA. In other embodiments, drive lines 44 can be made from a flexible tube, a single solid core line, a linkage, such as a chain or a linkage of universal joints, or other flexible or hinged members made from any of the above discussed materials. The diameter of drive lines 44 is in part dependent upon the materials used to make the drive lines and the size of the system. However, in some embodiments, the maximum or minimum diameter of each drive line 44 can be greater than, less than, or equal to 2 mm, 4 mm, 6 mm, 8 mm, 10 mm, 15 mm, or 20 mm or in a range between any two of the foregoing. Other dimensions can also be used.

As used herein, the term "diameter," whether in reference to the size of a drive line or other component (e.g., an opening), is not limited to the measurement of circular or spherical components. Rather, whether circular, oval or oblong, rectangular, angle or jagged, or a combination thereof, the diameter of the component refers to a (cross-sectional) measurement between opposing sides and/or the (maximum or minimum) distance between the opposing sides.

In one embodiment, at least a portion of the length of each drive line 44 is sufficiently flexible so that the flexible portion of each drive line 44 can be twisted under torsion about a longitudinal axis of each drive line 44 over an angle of at least 15°, 25°, 45°, 90°, 180°, 360°, 720° or more without plastic deformation of drive line 44. In other embodiments, at least a portion of the length of each drive line 44 is sufficiently flexible so that the flexible portion of each drive line 44 can be bent or folded relative to a linear longitudinal axis of drive line 44 over an angle α (FIG. 3) of at least 15°, 25°, 45°, 90°, 135°, 180°, 270°, or 360° or more without plastic deformation of drive line 44. Expressed in other terms, each drive line 44 or the flexible portion of each drive line 44 can have a bend radius wrapped 180° without plastic deformation in a range between about 2 cm to about 100 cm with about 6 cm to about 80 cm, about 10 cm to about 60 cm, or about 10 cm to about 40 cm being more common. Other flexibilities can also be used. As noted above, the entire length of each drive line 44 need not be flexible. For example, a percentage of the entire length of each drive line 44, such as at least or not to exceed 30%, 40%, 50%, 60%, 70%, 80%, 90% or more of drive line 44, could have the above flexible properties while the remainder is rigid or at least more rigid. In other embodiments, the entire length of drive line 44 can have the desired flexible properties.

As discussed below in greater detail, ties 45 are used in part to maintain at least portions of drive lines 44A and 44B in laterally spaced apart positions during operation of fluid mixing system 10. Because ties 45 are typically under compression between drive lines 44 during operation, ties 45 are typically more rigid than drive lines 44 and are typically made from a metal, polymer, ceramic, composite or other material. In the embodiment depicted in FIGS. 5 and 6, each tie 45 comprises an elongated brace 190 having a first end 191 and an opposing second end 192. Disposed at opposing ends 191 and 192 are U-shaped guides 193A and 193B, respectively. Each guide 193 has a U-shaped seat 194 configured to receive a drive line 44 and has an outside shoulder 195. Each tie 45 also includes a pair of fasteners 196A and 196B. Each fastener 196 comprises a back 198 and a pair of arms 200A and B projecting therefrom. A lip 202A and B inwardly projects from each arm 200A and B, respectively. A channel 203 is bounded between arms 200.

During use, drive lines 44A and 44B are received within seat 194 of guides 193A and B, respectively. Fasteners 196A and B are then passed over guides 193A and B, respectively, so that drive lines 44A and 44B are received within corresponding channels 203. Fasteners 196 are advanced until lips 202 resiliently snap behind outside shoulder 195. In this position, fasteners 196 are locked to guides 193 and drive lines 44 are compressed between fasteners 196 and guides 193 so that tie 45 is held fixed on each drive line 44A and 44B. This process is repeated for subsequent ties 45 at spaced apart locations along drive lines 44A and 44B.

It is appreciated that ties 45 can have a variety of different configurations and can be attached to drive lines 44A and B using a variety of different fastening techniques. For example, ties 45 could be crimped, welded, over molded, or adhered to drive lines 44. In other embodiments, threaded fasteners, clamps, press fit connections, screws, bolts, or the like can be used to secure ties 45 to drive lines 44A and B. In other embodiments, each drive line 44A and B can each comprise a plurality of separate line portions where free ends of adjacent line portions are separately secured to opposing sides of each tie 45.

The distance at which drive lines 44A and B are held spaced apart by ties 45 can vary based on factors such as the size of container 18 and the speed at which drive lines 44 are rotated. In some common embodiments, ties 45 are configured to maintain drive lines 44 spaced apart by a distance greater than, less than, or equal to 2 cm, 4 cm, 6 cm, 8 cm, 11 cm, 14 cm, 17 cm, 20 cm, 25 cm or in a range between any two of the foregoing. Other dimensions can also be used. The spacing between ties 45 can also vary based on system parameters and operating conditions. In some common embodiments, a plurality of ties 45 are spaced apart along the length of drive lines 44 by a distance greater than, less than, or equal to 5 cm, 8 cm, 11 cm, 14 cm, 17 cm, 20 cm, 25 cm or in a range between any two of the foregoing. The spacing can be consistent or varied between different pairs of ties 45.

Figure 5:
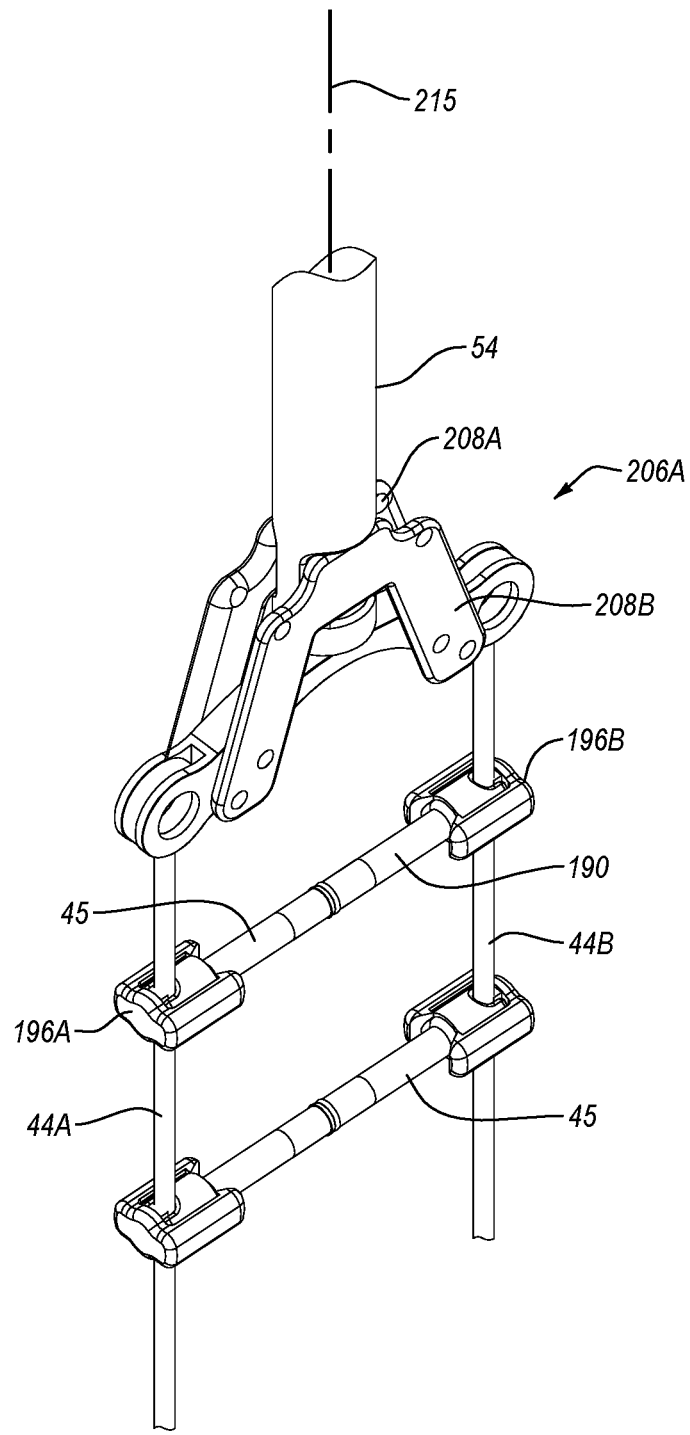
FIG. 5 is an enlarged perspective view of an upper end of the mixing assembly shown in FIG. 3.
Figure 6:
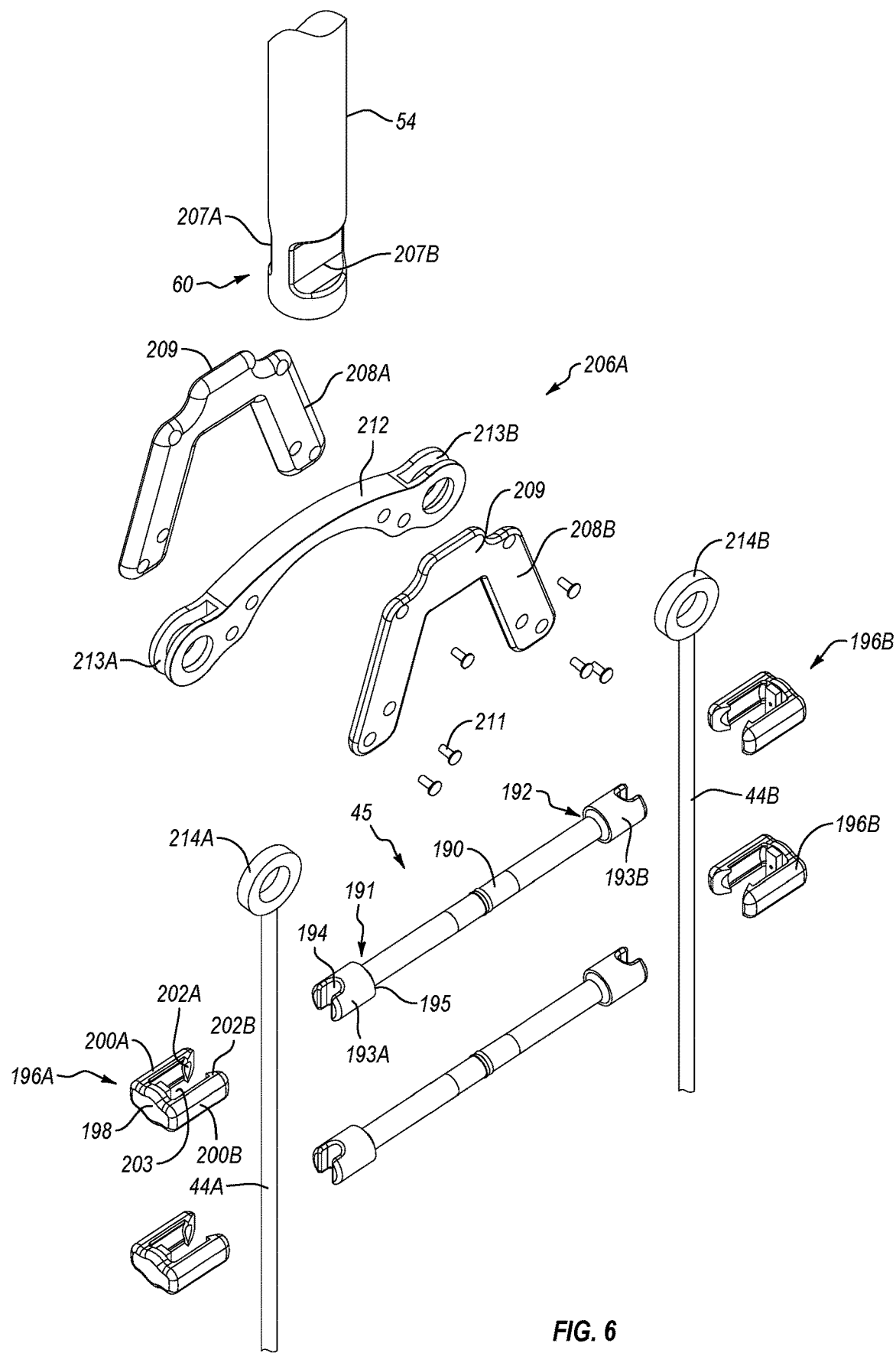
FIG. 6 is an exploded view of the upper end of the mixing assembly shown in FIG. 5.

As depicted in FIG. 2, a mount 206A is used to secure first ends 70 of drive lines 44 to hub 54 of rotational assembly 42A while a mount 206B is used to secure second ends 72 of drive lines 44 to hub 54 of rotational assembly 42B. As depicted in FIGS. 5 and 6, in the current embodiment mount 206A comprises U-shaped arms 208A and 208B each having a central portion 209 that is received within corresponding slots 207A and 207B formed on opposing sides of second end 60 of hub 54. Fasteners 211, such as screws, bolts, rivets or the like, secure arms 208A and B together so that hub 54 is sandwiched therebetween and securely fixed to arms 208. An elongated support 212 having slots 213A and B formed on opposing ends is also sandwiched between arms 208A and B so as to extend between the opposing ends of arms 208. Support 212 is also secured to arms 208A and B by fasteners 211. Mounted on first end 70 of each drive line 44A and B is a bushing 214A and 214B, respectively. Bushing 214 can be secured to drive lines 44 using conventional techniques such as welding, over molding, crimping, press fit, fastener or the like. Bushing 214A and B are rotatably secured within slots 213A and B, respectively, on support 212. Support 212 can be sized to that support 212 holds first ends 70 of drive lines 44 at the spaced apart distance discussed above with regard to ties 45.

Figure 10:
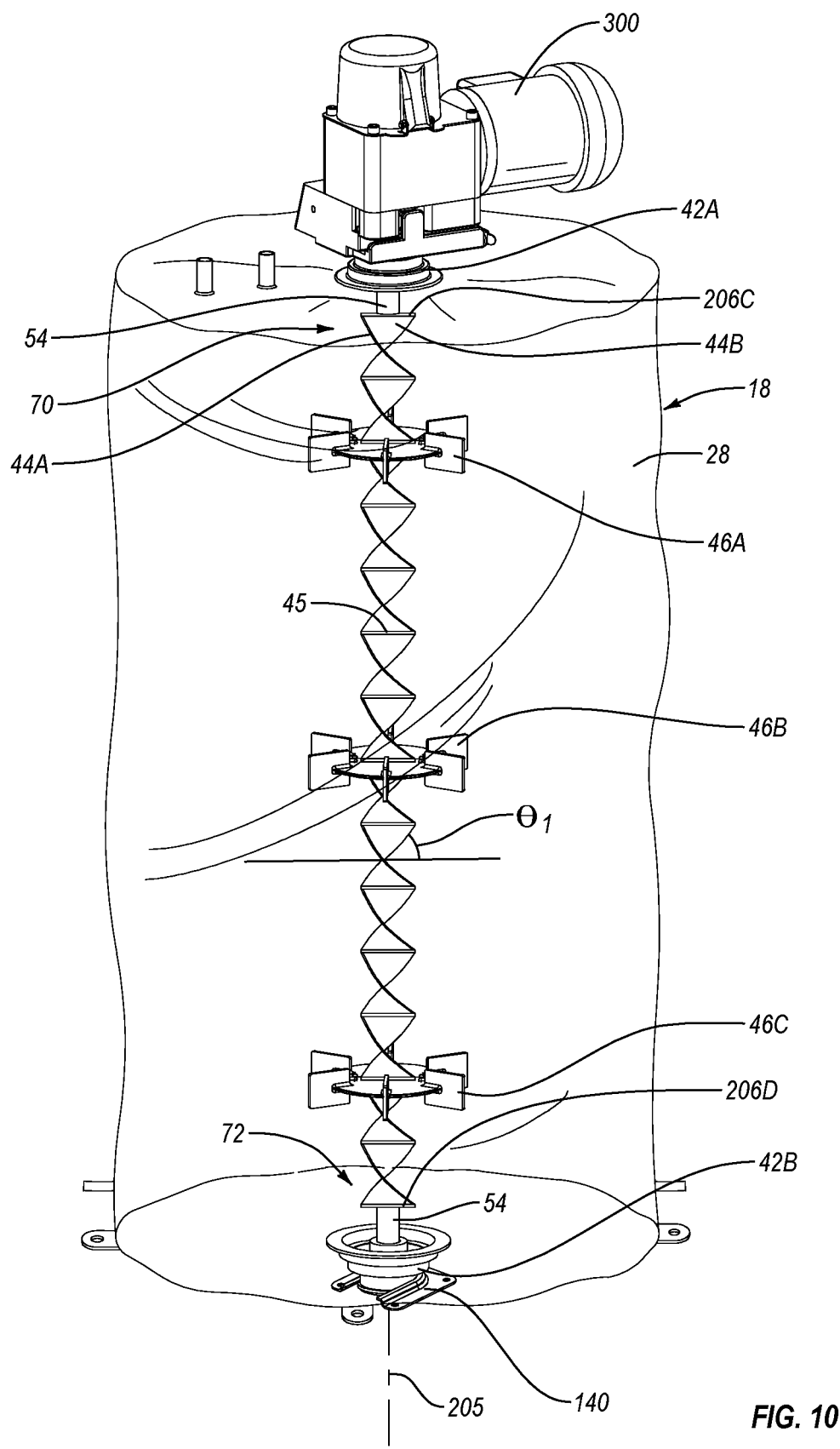
FIG. 10 is a perspective view of the container assembly shown in FIG. 2 coupled with the drive motor assembly and retainer shown in FIG. 1.

As a result of the above configuration, drives lines 44 are secured to hub 54 so that as hub 54 is rotated, drive lines 44 concurrently rotate. In the embodiment depicted, drive lines 44 rotate about a longitudinal axis extending through hub 54 (FIG. 5). First ends 70 of drive lines 44 can also rotate relative to mount 206 so as to help reduce localized stress on drive lines 44 during operation. In alternative embodiments, however, drive lines 44 can be secured to hub 54 using a variety of different techniques and configurations. For example, mount 206 can be eliminated and first end 70 of drive lines 44 can be secured directly to hub 54. In other embodiments, mount 206 can have a variety of different configurations. For example, arms 208 can be eliminated and support 212 connected directly to hub 54 such as by welding, fasteners, press fitting, over molding or being integrally formed as a unitary piece with hub 54. For example, FIG. 10 shows mounts 206C and 206D each in the form of an elongated support outwardly extending from hubs 54 of rotational assemblies 42A and 42B, respectively. Furthermore, bushings 214 can be eliminated and first and second ends 70 and 72 of drive lines 44 can be securely fixed to opposing ends of supports 212, securely fixed directly to hubs 54 or securely fixed to other mount configurations. Other configurations can also be used.

As depicted in FIG. 2, mount 206B can have the same configurations as mount 206A and can be used in the same way to secure second ends 72 of drive lines 44 to hub 54 of rotational assembly 42B. Like elements between mount 206A and B are identified by like reference characters and the same alternatives as discussed above with regard to mount 206A are also applicable to mount 206B.

Figure 7:
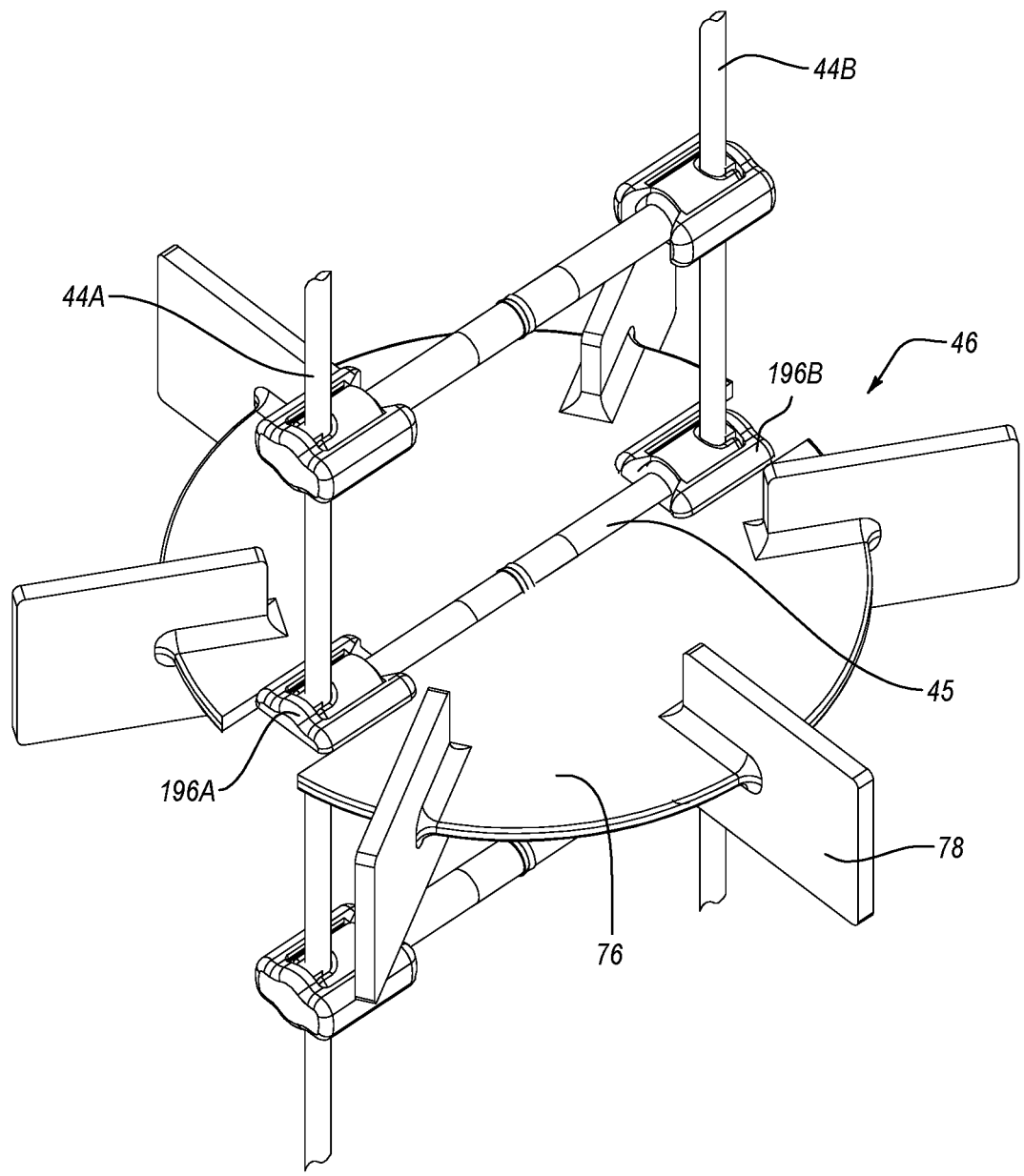
FIG. 7 is a perspective view of an impeller of the mixing assembly shown in FIG. 3.

Although not always required, in the embodiment depicted in FIG. 2, mixing assembly 40 also includes a plurality of mixing elements secured to drive lines 44A and B. In one embodiment, each mixing element can comprise an impeller 46 having a central hub 76 that spans between drive lines 44A and B and has a plurality of blades 78 radially outwardly projecting therefrom. Hub 76 can have a variety of different configurations. For example, as depicted in FIG. 7, hub 76 can simply comprise a tie 45 secured to drives lines 44A and B as discussed above and having a flange 77 outwardly projecting therefrom from which blades 78 project. The alternative tie designs discussed above and used in conjunction with flange 77 or without flange 77 can also be used. In other embodiments, tie 45 can be eliminated from hub 76 and hub 76 can simply comprise a plate or other structure that spans between drive lines 44A and B and is secured to drive lines 44 at desired locations by crimping, welding, adhesive or by using a set screw, clamp, fastener or other securing techniques. In yet other embodiments, each drive line 44A and B can each comprise a plurality of separate line portions where free ends of adjacent line portions are separately secured to opposing sides of each impeller 46. Other configurations can also be used.

It is appreciated that a variety of different numbers and configurations of blades 78 can be mounted on hub 76. Blades 78 can be rigidly fixed to hub 76 or can be pivotably coupled to hub 76. Examples of impellers having blades that are hingedly coupled to a hub are disclosed in US Patent Publication No. 2015/0117142, published Apr. 30, 2015 which is incorporated herein by specific reference. Although three impellers 46 are shown in FIG. 3, it is appreciated that impellers 46 can be positioned at any position along the length of drive lines 44 and that any number of mixing elements/impellers 46, such as 1, 2, 4, 5, or more, can be positioned along drive lines 44. In one embodiment of the present invention, the inventive system can be easily customized by choosing the type of mixing element/impeller, the number of mixing elements/impellers, and the location of mixing elements/impellers that are placed along drive lines 44 during assembly.

Impellers 46 disclosed herein and the alternatives discussed relative thereto are examples of mixing elements. Mixing elements, however, also include other structures that can be mounted on drive lines 44 that can function to mix fluid when rotated but which would not normally be considered an impeller. Examples of such other mixing elements can include paddles, stir bars, fins, blades, baffles and other structures that can be mounted directly or indirectly to drive lines 44 for use in mixing.

Figure 8:
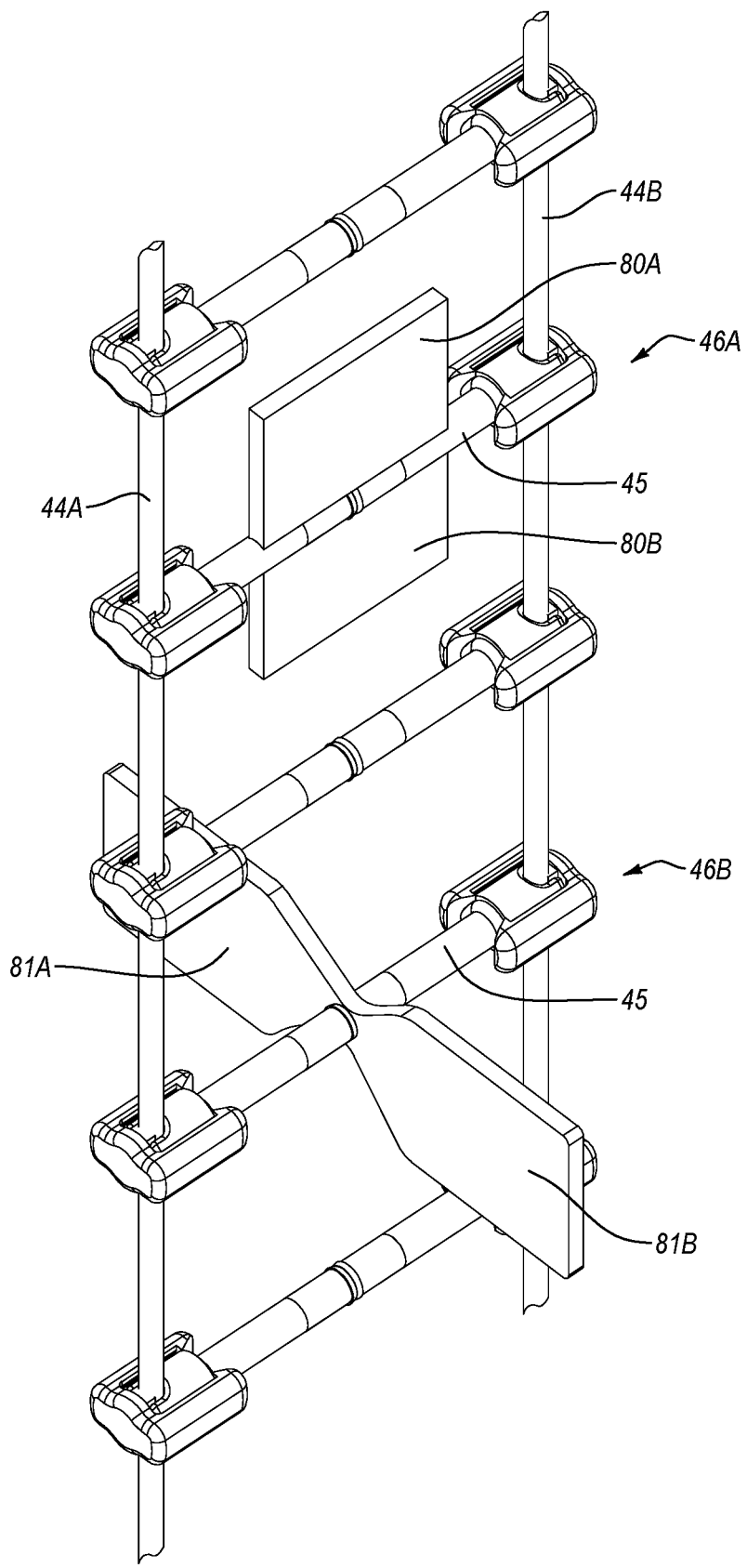
FIG. 8 is a perspective view of a portion of a mixing assembly having alternative impellers.

Depicted in FIG. 8 is one alternative embodiment of an impeller 46A that includes a tie 45 having blades 80A and 80B vertically outwardly projecting therefrom. An impeller 46B is also depicted that includes a tie 45 having blades 81A and 81B laterally outwardly projecting therefrom. Alternative configurations for tie 45 as discussed above, can also be used can also be used in conjunction with blades 80 and 81. In yet other embodiments, mixing assembly 40 can exclude the use of any impellers or mixing elements. For example, when relatively small containers 18 are used, drive lines 44 and ties 45 can be independently sufficient to achieve the necessary mixing.

FIG. 2 shows container assembly 16 including mixing assembly 40 in a relaxed vertically extended state. Drive lines 44A and B are laterally spaced apart, i.e., drive lines 44 are disposed side-by-side with first ends 70 being disposed toward upper end 22 of container 18 and second ends 72 being disposed toward lower end 24 of container 18. In the depicted embodiment, the full length of drive lines 44 are disposed within compartment 28 of container 18, drive lines 44 are spaced apart a substantially constant distance along their full lengths, and drive lines 44 are disposed in substantially parallel alignment. The term "substantially" as used herein is intended to account for slight offsets resulting from conventional manufacturing processes and tolerances. As discussed below in more detail, in alternative embodiments drives lines 44 need not have a constant separation along their length and need not be in parallel alignment when in the vertically extended relaxed state.

As depicted in FIG. 3, mixing assembly 40 is used in conjunction with drive shaft 17. Drive shaft 17 has a first end 84 and an opposing second end 86. Formed at first end 84 is a frustoconical engaging portion 88 that terminates at a circular plate 90. Notches 92 are formed on the perimeter edge of circular plate 90 and are used for engaging drive shaft 17 with a drive motor assembly as will be discussed below.

Formed at second end 86 of drive shaft 362 is driver portion 68. Driver portion 68 has a non-circular transverse cross section complementary to opening 66 of hub 54 (FIG. 4) so that it can facilitate locking engagement within opening 66 of hub 54. In the embodiment depicted, driver portion 68 has a polygonal transverse cross section. However, other non-circular shapes can also be used. It is also appreciated that other releasable locking mechanisms can be used to engage drive shaft 17 with hub 54. For example, a bayonet connection, threaded connection, clamp, or fastener could be used.

Returning to FIG. 1, container station 14 comprises a support housing 100 supported on a cart 102. Support housing 100 has a substantially cylindrical sidewall 104 that extends between an upper end 106 and an opposing lower end 108. Lower end 108 has a floor 110 mounted thereto. As a result, support housing 100 has an interior surface 112 that bounds a chamber 114. An annular lip 116 is formed at upper end 106 and bounds an opening 118 to chamber 114. As discussed above, chamber 114 is configured to receive container assembly 16 so that container 18 is supported therein.

Although support housing 100 is shown as having a substantially cylindrical configuration, in alternative embodiments support housing 100 can have any desired shape capable of at least partially bounding a compartment. For example, sidewall 104 need not be cylindrical but can have a variety of other transverse, cross sectional configurations such as square, rectangular, polygonal, elliptical, or irregular. Furthermore, it is appreciated that support housing 100 can be scaled to any desired size. For example, it is envisioned that support housing 100 can be sized so that chamber 114 can hold a volume of less than 50 liters, more than 1,000 liters or any of the other volumes or range of volumes as discussed above with regard to container 18. Support housing 100 is typically made of metal, such as stainless steel, but can also be made of other materials capable of withstanding the applied loads of the present invention.

With continued reference to FIG. 1, sidewall 104 of support housing 100 has an enlarged access 120 at lower end 108 so as to extend through sidewall 104. A door 122 is hingedly mounted to sidewall 104 and can selectively pivot to open and close access 120. A latch assembly 124 is used to lock door 122 in the closed position. An opening 126, which is depicted in the form of an elongated slot, extends through door 122. Opening 126 is configured to align with ports 31 (FIG. 2) of container assembly 16 when container assembly 16 is received within chamber 114 so that ports 31 project into or can otherwise be accessed through opening 126. In some embodiments, a line for carrying fluid or gas will be couple with port 31 and can extend out of chamber 114 through opening 126. As previously mentioned, any number of ports 31 can be formed on container 18 and thus any number of separated lines can pass out through opening 126 or through other openings formed on support housing 100. Alternatively, different types of probes, sensors, inserts, connectors, or the like may be coupled with ports 31 which can be accessed through opening 126 or other openings.

In one embodiment of the present invention means are provided for regulating the temperature of the fluid that is contained within container 18 when container 18 is disposed within support housing 100. By way of example and not by limitation, sidewall 104 can be jacketed so as to bound one or more fluid channels that encircle sidewall 104 and that communicate with an inlet port 130 and an outlet port 132. A fluid, such as water or propylene glycol, can be pumped into the fluid channel through inlet port 130. The fluid then flows in a pattern around sidewall 104 and then exits out through outlet port 132.

By heating or otherwise controlling the temperature of the fluid that is passed into the fluid channel, the temperature of support housing 100 can be regulated which in turn regulates the temperature of the fluid within container 18 when container 18 is disposed within support housing 100. In an alternative embodiment, electrical heating elements can be mounted on or within support housing 100. The heat from the heating elements is transferred either directly or indirectly to container 18. Alternatively, other conventional means can also be used such as by applying gas burners to support housing 100 or pumping the fluid out of container 18, heating the fluid and then pumping the fluid back into container 18. When using container 18 as part of a bioreactor or fermentor, the means for heating can be used to heat the culture within container 18 to a temperature in a range between about 30° C. to about 40° C. Other temperatures can also be used.

As will be discussed further below, a retainer 140 is centrally mounted on the interior surface of floor 110 of support housing 100. Retainer 140 has a U-shaped slot 142 that is bounded by an inwardly projecting U-shaped catch lip 144. Retainer 140 is configured so that when container assembly 16 is received within chamber 114 of support housing 100, second rotational assembly 42B can be manually slid into slot 142 (FIG. 3) so that mounting flange 53 of second rotational assembly 42B is captured within slot 142 below catch lip 144, thereby securing second rotational assembly 42B to retainer 140 and preventing rotational assembly 42B from being raised vertically relative to retainer 140. It is appreciated that the function of retainer 140 is to releasably engage second rotational assembly 42B and, as such, the configuration of retainer 140 can change as the configuration of rotational assembly 42B changes. Furthermore, retainer can have different slot configurations and can be in the form of a variety of different clamps, ties, fasteners or the like that are designed to engage rotational assembly 42B in its present form or in a modified form. It is likewise appreciated that second rotational assembly 42B can be attached to retainer 140 by reaching in through access 120 on sidewall 104 of support housing 100.

As depicted in FIG. 1, docking station 12 comprises a stand 134, an adjustable arm assembly 136 coupled to stand 134 and a drive motor assembly 300 mounted on arm assembly 136. Drive motor assembly 300 is used in conjunction with drive shaft 17 (FIG. 3) and can be used for mixing and/or suspending a culture, solution, suspension, or other liquid within container 18 (FIG. 2). Turning to FIG. 3, drive motor assembly 300 comprises a housing 304 having a front face 305 that extends from a top surface 306 to an opposing bottom surface 308. An opening 310 extends through housing 304 from top surface 306 to bottom surface 308. A tubular motor mount 312 is rotatably secured within opening 310 of housing 304. Upstanding from motor mount 312 is a locking pin 316. A drive motor 314 is mounted to housing 304 and engages with motor mount 312 so as to facilitate select rotation of motor mount 312 relative to housing 304. Drive shaft 17 is configured to pass through motor mount 312 so that engaging portion 88 of drive shaft 17 is retained within motor mount 312 and locking pin 316 of motor mount 312 is received within notch 92 of drive shaft 17. As a result, rotation of motor mount 312 by drive motor 314 facilitates rotation of drive shaft 17. A removable cap 313 is used to hold drive shaft 17 on motor mount 312. Further discussion of drive motor assembly 300 and how it engages with drive shaft 17 and alternative designs of drive motor assembly 300 are discussed in US Patent Publication No. 2011/0188928, published Aug. 4, 2011 which is incorporated herein in its entirety by specific reference.

Figure 9:
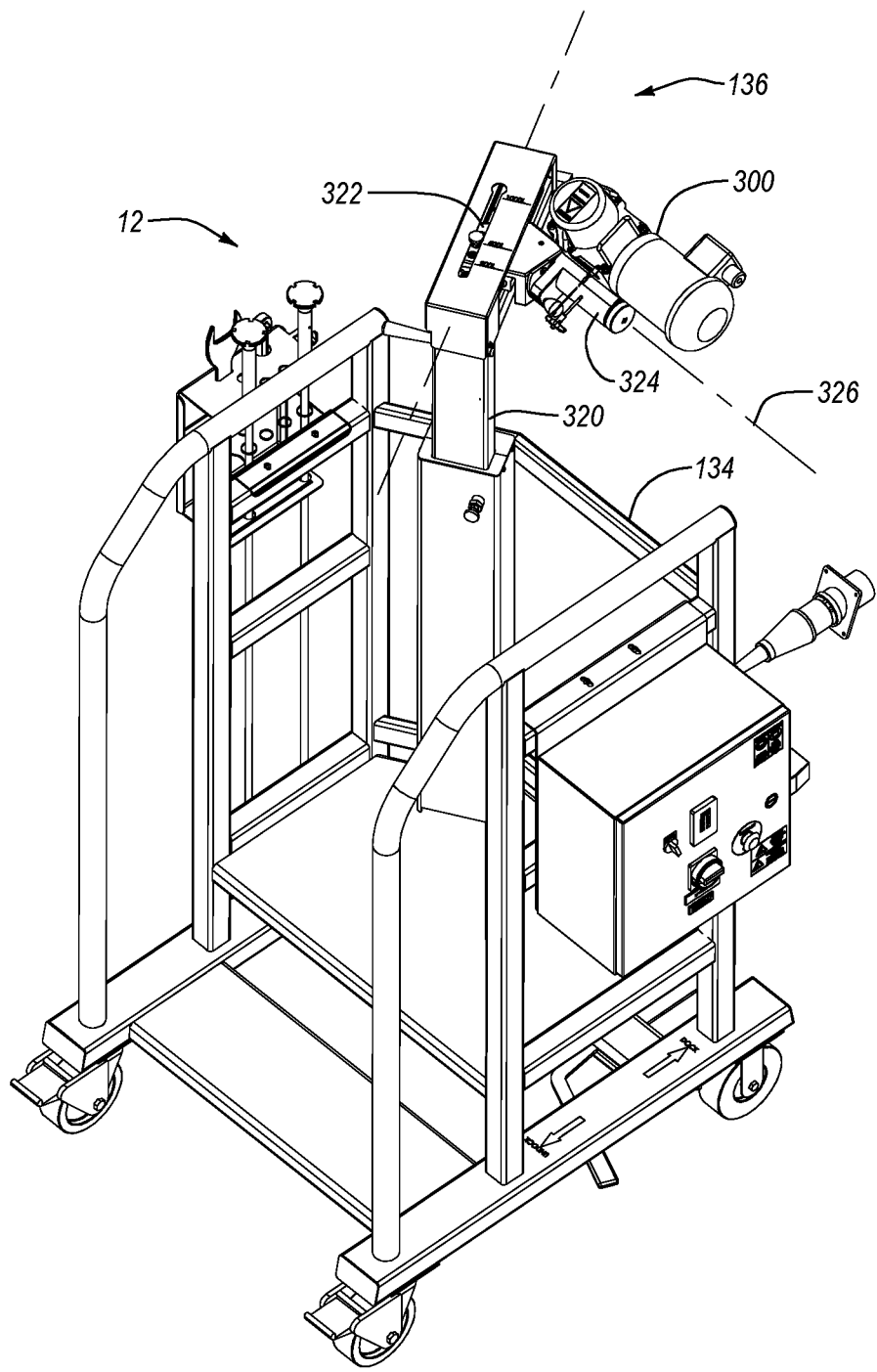
FIG. 9 is a back perspective view of the docking station shown in FIG. 1.

As depicted in FIG. 9, arm assembly 136 is used to adjust the position of drive motor assembly 300 and thereby also adjust the position of drive shaft 17. Arm assembly 136 comprises a first arm 320 mounted to stand 134 that vertically raises and lowers, a second arm 322 mounted to the first arm 320 that slides horizontally back and forth, and a third arm 324 mounted to second arm 322 that rotates about a horizontal axis 326. Drive motor assembly 300 is mounted to third arm 324. Accordingly, by movements of arms 320, 322, and/or 324, drive motor assembly 300 can be positioned in any desired location or orientation relative to support housing 100 and container assembly 16. For example, drive motor assembly 300 can be positioned so that drive shaft 17 is centered and vertically oriented when connected with container assembly 16. In other embodiments, drive shaft 17 can be oriented at an angle, such as in a range between 10° to 30° from vertical when connected with container assembly 16. Further discussion and alternative embodiments with regard to docking station 12, arm assembly 136, and container station 14 is provided in US Patent Publication No. 2011/0310696, published Dec. 22, 2011, which is incorporated herein in its entirety by specific reference.

During use, container station 14 and docking station 12 are removably coupled together as shown in FIG. 1. One example of how docking station 12 and container assembly 16 can be coupled together is disclosed in US Patent Publication No. 2011/0310696 which was previously incorporated by reference. Other methods can also be used. Either before or after coupling together container station 14 and docking station 12, container assembly 16 (FIG. 2) is positioned within chamber 114 of support housing 100 and second rotational assembly 42B is secured to retainer 140 as discussed above.

In this position, arm assembly 136 is used to properly position drive motor assembly 300 so that first rotational assembly 42A can be coupled with drive motor assembly 300. Specifically, as depicted in FIG. 3, housing 304 of drive motor assembly 300 has a U-shaped receiving slot 330 that is recessed on a front face 305 and bottom surface 308 so as to communicate with opening 310 extending through housing 304. Receiving slot 330 is bounded by an inside face 332 on which a U-shaped catch slot 334 is recessed. As shown in FIG. 1, a door 336 is hingedly mounted to housing 304 and selectively closes the opening to receiving slot 330 from front face 305. As depicted in FIG. 3, to facilitate attachment of rotational assembly 42A to housing 304, with door 336 rotated to an open position, rotational assembly 42A is horizontally slid into receiving slot 330 from front face 305 of housing 304 so that mounting flange 53 that is radially outwardly extending from the upper end of rotational assembly 42A is received and secured within catch slot 334. First rotational assembly 42A is advanced into receiving slot 330 so that opening 66 of rotational assembly 42A aligns with the passage extending through motor mount 312. Door 336 (FIG. 1) is then moved to the closed position and secured in place by a latch or other locking mechanism so that first rotational assembly 42A is locked to drive motor assembly 300.

Rotational assemblies 42A and 42B are now secured to drive motor assembly 300 and retainer 140, respectively, as shown in FIG. 10. Arm assembly 136 (FIG. 5) can now be used to add slack or tension to flexible drive lines 44 by lowering or raising drive motor assembly 300 to which rotational assembly 42A is coupled. Likewise, arm assembly 136 can be used to adjust the orientation of drive lines 44. For example, by adjusting the position of drive motor assembly 300, drive lines 44 can be adjusted so as to be centered within support housing 100 and vertically oriented or drive lines 44 can be oriented at an angle, such as in a range between 10° to 30° from vertical. Other positions and orientations can also be used.

Once first rotational assembly 42A is secured to drive motor assembly 300, drive shaft 17 can be advanced down through motor mount 312 of drive motor assembly 300 and into opening 66 of rotational assembly 42A so that drive shaft 17 engages with hub 54. Liquid and other components can be delivered into container 18. For example, where container 18 is functioning as a bioreactor or fermentor, cells or microorganisms along with media, nutrients and other standard components can be added to container 18. As previously discussed, other liquids such as chemicals, medications, beverages, food products, or the like can also be processed. Drive motor 314 can be activated so as to rotate drive shaft 17 which in turn begins the rotation of hub 54 of first rotational assembly 42A, drive lines 44, and impellers 46. Rotation of drive lines 44 and impellers 46 facilitates mixing and/or suspension of the liquid and components contained within container 18. Where needed, the liquid can be concurrently sparged with a gas while mixing.

Drive lines 44 are typically sized so that they can be slack when container assembly 16 is secured to support housing 100 and drive motor assembly 300. The slack or tension in drive lines 44 can be adjusted by using arm assembly 136 (FIG. 9) to selectively raise or lower first rotational assembly 42A. Because drive lines 44 are slack and made of a flexible material, drive lines 44 will twist into a helical configuration along their length during operation as shown in FIG. 10, i.e., drive lines 44A and B form a double stranded helix. That is, first end 70 of drive lines 44 begin to rotate concurrently with the rotation of hub 54 of first rotational assembly 42A. However, as a result of the resistance produced by the liquid on impellers 46, drive lines 44 and ties 45 and the friction resistance produced by hub 54 of second rotational assembly 42B, drive lines 44A and B begin to twist into the helical configuration during operation so as to cause each drive line 44 to come under torsion. In addition, as drive lines 44A and B twist into the helical configuration, the vertical length of drive lines 44 is shorted. However, because second end 72 of drive lines 44 are restrained from being raised vertically both because of the fluid within container 18 and because of retainer 140, drive lines 44 can twist to the extent that slack is removed from drive lines 44 but lines 44 are thereafter restrained from being further shortened along the vertical length which places drive lines 44 in tension. Once sufficient torsion is placed on drive lines 44 to overcome the fluid resistance and friction force, the entire length of drives lines 44 rotate within container 18.

It is appreciated that a majority of the fluid resistance is produced by impellers 46 and that the torsional force produced on drive lines 44 varies at sections between impellers 46. For example, with reference to FIG. 2, the sections of drive lines 44 between first rotational assembly 42A and first impeller 46A is generally subject to the highest torsion force because that section of drive lines 44 is subjected to the resistance produced by the portion of mixing assembly 40 that extends from impeller 46A to second rotational assembly 42B, i.e., includes each of impellers 46A-46C. In contrast, the section of drive lines 44 between impeller 46C and rotational assembly 42B is only subject to the resistance produced by mount 206B and hub 54 of second rotational assembly 42B. As such, during operation of the current embodiment the torsion on the lower section of drives lines 44 is less than the torsion on the upper section of drive lines 44.

Drive lines 44 are, in part, specifically designed to twist into a helical configuration to minimize the tension and torsion force that lines 44 are subject to during operation. That is, as drive lines 44 twist into the helical configuration, as discussed above and depicted in FIG. 10, a portion of the torsion and tension that is applied to drive lines 44 is converted to a vector force that tries to push drive lines 44A and B together. This vector force is applied to the opposing ends of ties 45 which, as a result, place ties 45 under compression. Ties 45, however, are sufficiently rigid and have sufficient strength to carry the compressive load without failure and thus maintain the spacing between drive lines 44.

It is typically desirable that drive lines 44 have a length and flexibility that permits drive lines 44 to twist into a helical configuration so that an inside angle $\theta 1$, as shown in FIG. 10, is formed between lines 44 and a plane 204 that extends normal to an axis of rotation 205 of drive lines 44. Angle $\theta 1$ is typically in a range between 20° and 70° and more commonly in a range between 30° and 60° or 35° and 55°. In other embodiments, the angle $\theta 1$ can be greater than, less than, or equal to 20°, 30°, 40°, 50°, 60°, 70° or in a range between any two of the foregoing. Other angles can also be used. As angle $\theta 1$ decreases from 90°, more of the tension and torque on drive lines 44 is converted to the vector force as discussed above. As a result, by designing mixing assembly 40 to operate at lower angles for angle θ1, dive lines 44 can be made thinner or from less robust material and yet still withstand the required loads. Accordingly, drive lines 44 can be made lighter and/or less expensively. Ties 45 also function to maintain spacing between drive lines 44 which helps prevent drive lines 44 from spooling up on themselves, i.e., twisting together, which can destabilize the mixing and result in failure in the mixing assembly. However, if angle θ1 gets too small, there is an increased risk that the combined drive lines 44 can still spool or twist together. Thus, it is desired to maintain drive lines 44 between a preferred range of angles for angle θ1.

In one embodiment, container assembly 16 can be configured and operated within support housing 100 so that drive lines 44 and the helix formed thereby remain substantially vertically orientated prior to and during operation. In one alternative, however, retainer 140 could be positioned offset from the center of the floor of support housing 100 and second rotational assembly 42B could be complementarily offset from the center of the floor of container 18. In turn, arm assembly 136 (FIG. 9) can be used to adjust the angle and lateral position of first rotational assembly 42A. As such, the helix formed by drive lines 44 can be set to operate at an angle relative to vertical that is substantially less than, greater than, or equal to 5°, 10°, 15°, 20° or 25° or in a range between any two of the foregoing.

The inventive mixing assembly of having at least two flexible drive lines 44 held spaced apart during mixing has a number of unique advantages. For example, the mixing assembly remains flexible so that container assembly 16 can be collapsed and folded upon itself for easy sterilization, transportation and storage. The folded and collapsed container assembly can also be easily inserted into chamber 114 of support housing 100 even in low ceiling facilities.

The inventive system also solves many of the problems encounter by using the single flexible drive line system disclosed in International Publication No. WO 2013/151733, which is referenced in the background section of the present application. For example, one of the problems with the single flexible drive line system is that during operation the single flexible drive line can easily spool up on itself, i.e., twist into a knot at one or more locations along the length of the drive line. This spooling can result in failure of the system, i.e., rupture of the drive line and/or bag, and also disrupts uniform mixing of the fluid. Furthermore, the single drive line is subject to very high torsion and tension loads during fluid mixing. These loads significantly increase when it is necessary to mix large volumes of fluid at a rapid rate, such as when the bag is being used as fermentor. Although these problems can be at least partially overcome by increasing the stiffness and thickness of the single drive line, as the single drive line increases in size and stiffness, the bag becomes more difficult to fold, unwieldy to manage, and more expensive to produce.

In contrast, the inventive system having at least two laterally spaced apart drive lines 44 that concurrently rotate about a common axis of rotation significantly decreases the chance that drive lines 44 can spool up or twist together. Furthermore, as a result of spaced apart drive lines 44 twisting into a helical configuration during operation, the tension and torsion loads placed on drive lines 44 are reduced relative to the tension and torsion loads that would be placed on a single drive line. As a result, relative to a single drive line system, drive lines 44 can be made thinner, more flexible and/or with less expensive material so as to make the overall system lighter, more flexible and/or less expensive while maintaining high efficiency and reliability.

Although the above discussed embodiment and alternatives are possible configurations for the present invention, it is appreciated that a variety other configurations and methods can also be used. For example, in an alternative method of use as previously mentioned, a second drive shaft could be coupled with hub 54 of second rotational assembly 42B through a hole formed in floor 110 of support housing 100. Even in this embodiment, however, there could still be some helical twisting of drive lines 44. For example, the opposing ends of drive lines 44 could twist in opposite directions toward the middle of drive lines 44 or the rotation of hubs 54 could be staggered, i.e., one starts rotating before the other, so that again a common helix is formed along the length of drive lines 44.

In mixing system 10, docking station 12 is used which includes arm assembly 136. In this design, docking station 12 can be coupled with any number of different container stations 14 having a container assembly 16 therein. In an alternative embodiment, however, docking station 12 can be eliminated and arm assembly 136 can be mounted directly onto support housing 100. Alternative examples of arm assemblies and how they can be mounted onto support housing 100 is disclosed in US Patent Publication No. 2013/0101982, published on Apr. 25, 2013, which is incorporate herein in its entirety by specific reference.

Figure 11:
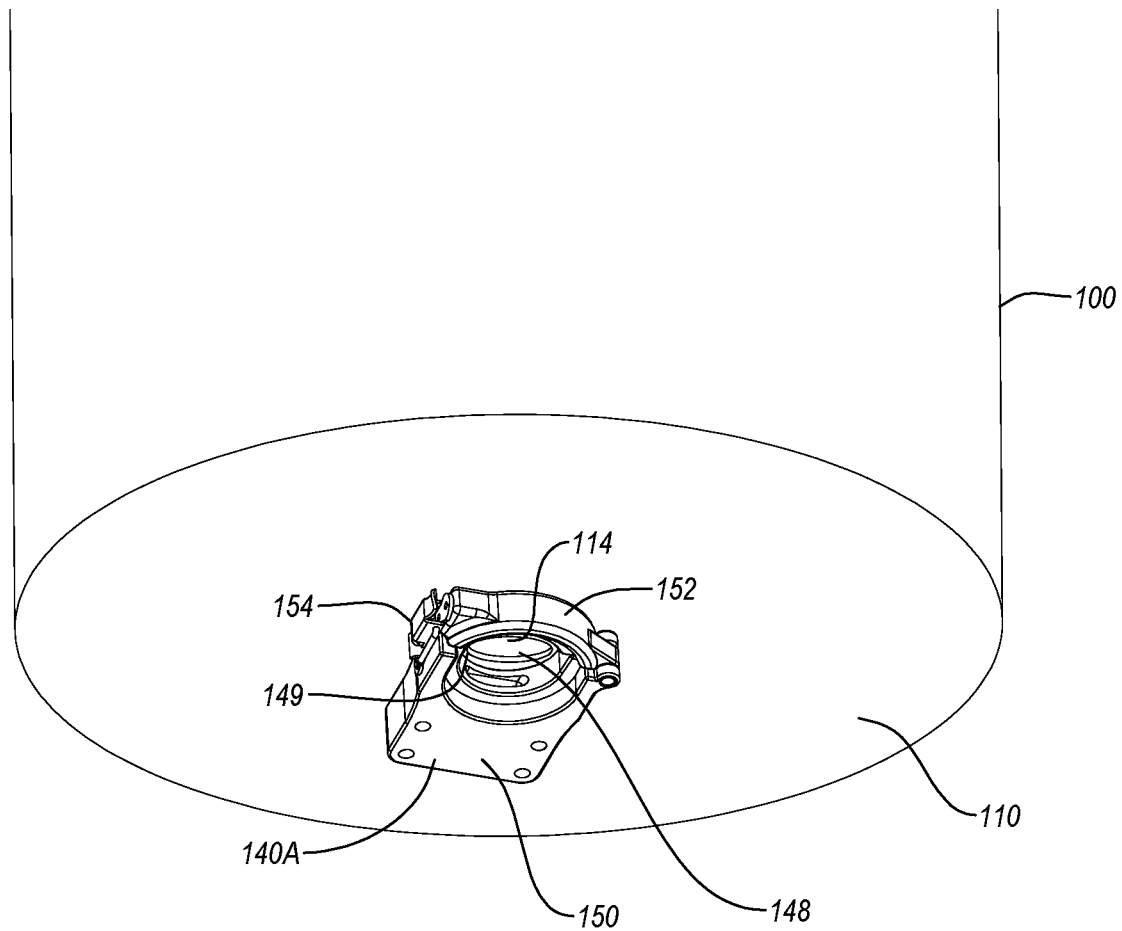
FIG. 11 is a bottom perspective view of an alternative embodiment of the support housing shown in FIG. 1 with a retainer mounted on the exterior surface of the floor.

In the above discussed embodiment depicted in FIG. 1, retainer 140 is mounted on the interior surface of floor 110 of support housing 100 for engaging with second rotational assembly 42B (FIG. 2). In an alternative embodiment as depicted in FIG. 11. A retainer 140A can be mounted on the exterior surface of floor 110 of support housing 100. A hole 148 centrally extends through floor 110 so as to communicate with chamber 114. In this embodiment, retainer 140A has an opening 149 that is bounded between a body 150 and a locking arm 152 hingedly mounted thereto. During use, with locking arm 152 in an open position, the free end of second rotational assembly 42B (FIG. 2) is passed down through hole 148 so as to be received within opening 149. Locking arm 152 is then moved to the closed position, as shown in FIG. 11, and secured in place by a latch 154. In this configuration, the end of second rotational assembly 42B is secured to retainer 140A. It is appreciated that retainers 140 and 140A can come in a variety of other configurations and need only be able to releasably engage the second rotational assembly 42B. In still other embodiments, the retainer need not be secured to support housing 100 but can be located on a separate structure at a position below support housing 100. Second rotational assembly 42B can be configured to pass down through hole 148 and engage with the retainer.

In one embodiment of the present invention, means are provided for holding the lower end 24 of container 18 stationary while flexible drive lines 44 is rotated within compartment 28 of container 18. Examples of this means includes retainer 140 mounted on the interior surface of floor 110, retainer 140A mounted on the exterior surface of floor 110 retainer 140A mounted on a separate structure located below floor 110, and other configurations of retainers that can be placed in the above locations. The means for holding can also comprise any number of conventional fastening techniques and separable interlocking structures that can be used to secure lower end 24 of container 18 within support housing 100. Such structures can include securing second rotational assembly 42B or some other structure secured to container 18 to support housing using screws, bolts, hooks, Velcro, i.e., hook and loop material, threaded connection, bayonet connection, clamps or the like.

Figure 12:
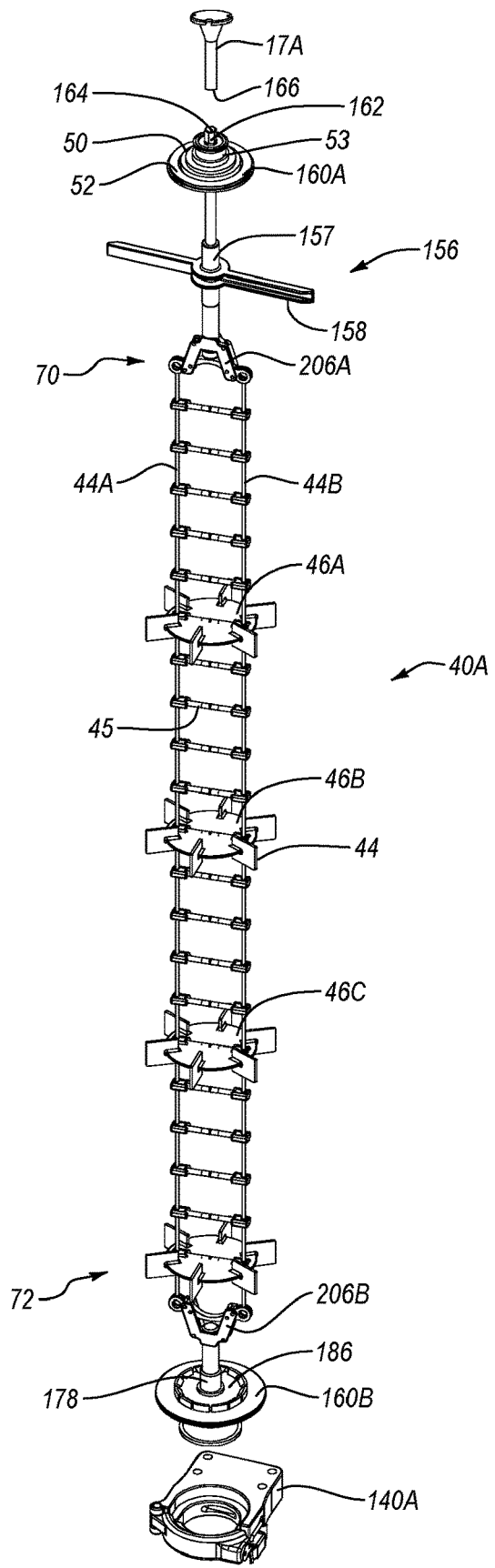
FIG. 12 is a perspective view of an alternative embodiment of a mixing assembly that can be used with the container shown in FIG. 2.

Depicted in FIG. 12 is an alternative embodiment of a mixing assembly 40A. Like elements between mixing assemblies 40 and 40A are identified by like reference characters. Mixing assembly 40A comprises a first rotational assembly 160A and a second rotational assembly 160B with drive lines 44A and B extending therebetween. First rotational assembly 160A has substantially the same configuration as first rotational assembly 42A and includes outer casing 50 having sealing flange 52 for securing to container 18 and mounting flange 53. First rotational assembly 160A has a hub 162 that rotates relative to casing 50. However, in contrast to having an opening 66 (FIG. 4) located at the end thereof, hub 162 includes an outwardly projecting stem 164 which forms another example of an engaging portion. Stem 164 has a non-circular transverse cross section, such as polygonal, so that a drive shaft 17A having a complementary socket 166, that replaces driver portion 68 (FIG. 3), can securely engage with and rotate hub 162.

Figure 13:
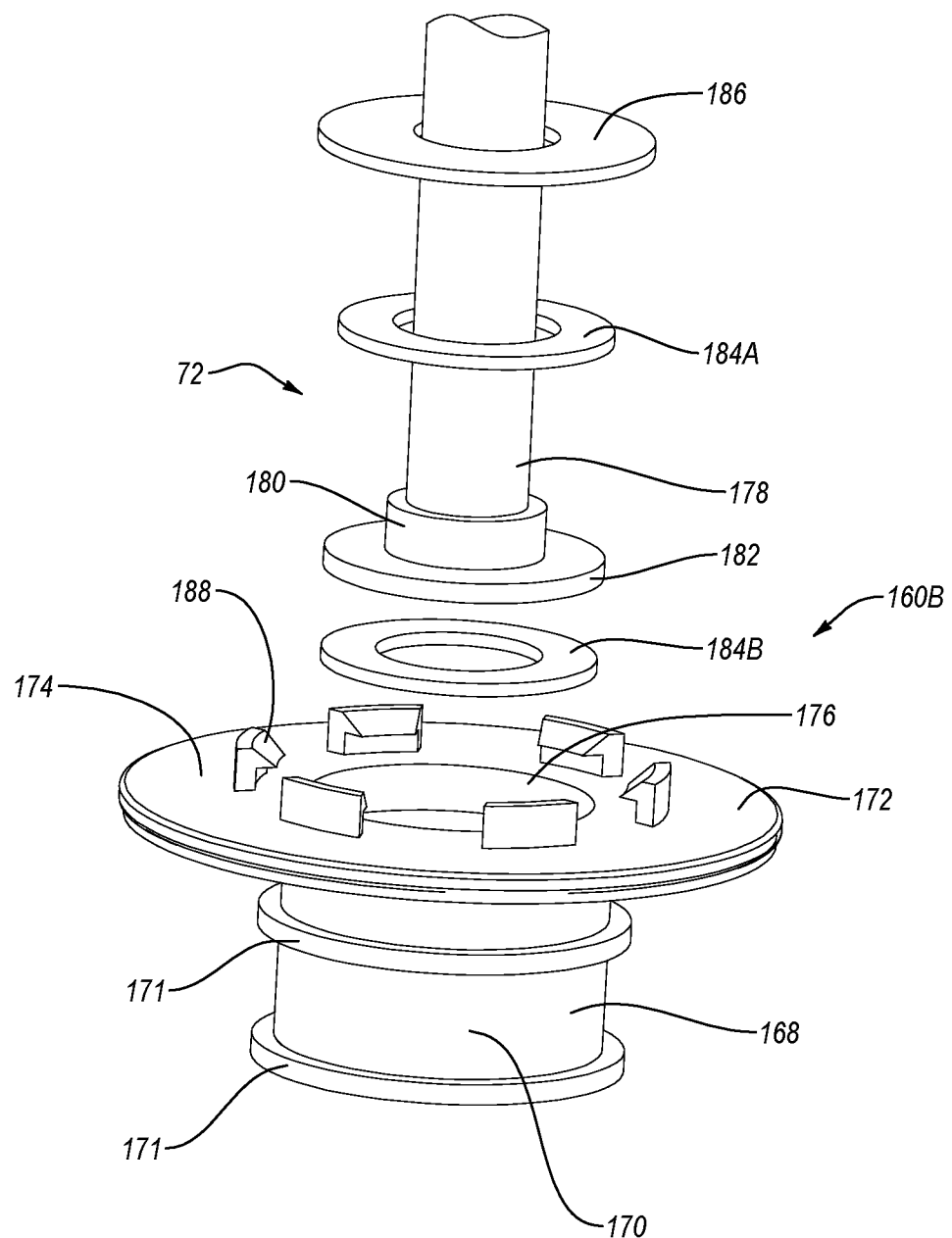
FIG. 13 is an exploded view of the lower rotational assembly shown in FIG. 12.

As depicted in FIG. 13, second rotational assembly 160B comprises an outer casing 168 that includes a cylindrical base 170 having one or more mounting flanges 171 radially outwardly projecting from a lower end thereof and an enlarged annular sealing flange 172 radially outwardly projecting from the upper end thereof. Base 170 and mounting flanges 171 are configured to be engaged by retainer 140A (FIG. 12). Sealing flange 172 is configured to secure to container 18, such as by welding, in the same manner as sealing flange 52 (FIG. 2). Outer casing 168 has a top surface 174 on which a cylindrical blind pocket 176 is formed.

Second rotational assembly 160B also includes a hub 178 having a base 180. Hub 178 also includes an annular flange 182 encircling and radially outwardly projecting from a lower end of base 180. Flange 182 is configured so that it can be rotatably received within blind pocket 176. Annular bearings 184A and 184B, such as roller thrust bearings, are also received within pocket 176 on opposing sides of flange 184 so that hub 178 can freely rotate relative to outer casing 168. A cover plate 186 encircles hub 178 and is positioned over bearing 184A. Cover plate 186 is secured in place by engaging with locking fingers 188 that project from top surface 174 at spaced apart locations around pocket 176. In this configuration, cover plate 186 retains hub 178 within outer casing 168. It is appreciated that because pocket 176 is blind, it is not necessary to position a seal between hub 178 and outer casing 168, although a seal can be used if desired so as to prevent fluid from entering pocket 176. It is also appreciated that the rotational assemblies can have a variety of other configurations.

Drive opposing ends 70 and 72 of drive lines 44A and B are connected to hubs 162 and 178, respectively, using mounts 206A and B. Other configurations of mounts discussed herein can be used or mounts 206 can be eliminated. Drive lines 44 are separated by ties 45 and have impeller 46 mounted thereon.

Returning to FIG. 12, disposed at an upper end of hub 162 is a foam breaker 156. Foam breaker 156 includes a hub 157 secured to hub 162 and a bar 158 that outwardly projects from opposing sides of hub 157. Foam breaker 156 rotates concurrently with hub 162 to break up foam that is formed at the upper end of container 18. It is appreciated that foam breaker 156 can come in a variety of different configurations.

In one embodiment of the present invention, means are provided for rotating first drive line 44A and second drive line 44B within compartment 28 of container 18. By way of example and not by limitation, such means can comprise drive shaft 17, 17A that is configured to engage the hub of one of the rotational assemblies and also includes drive motor assembly 300 that rotates drive shaft 17, 17A. The means for rotating also includes other structures that can be used to rotate the hub of one of the rotation assemblies. For example, the means could include a hub of a rotational assembly that projects out of container 18 and engages directly with drive motor assembly 300. Other configurations of drive shafts 17 and drive motor assemblies 300 having different interlocking features can also be used. The means also includes other non-drive shaft systems that can be used to rotate drive lines 44. For example, a gear assembly, belt, drive wheel, or other structures can be used to rotate the hub. Furthermore, magnetic drive systems placed outside of container 18 and operating with a corresponding component disposed within container 18 and coupled with drive lines 44 can be used to magnetically rotate drive lines 44. The means can also comprise other conventional systems used to drive impellers, stir bars, mixing paddles, and other stirring elements.

Figure 14:
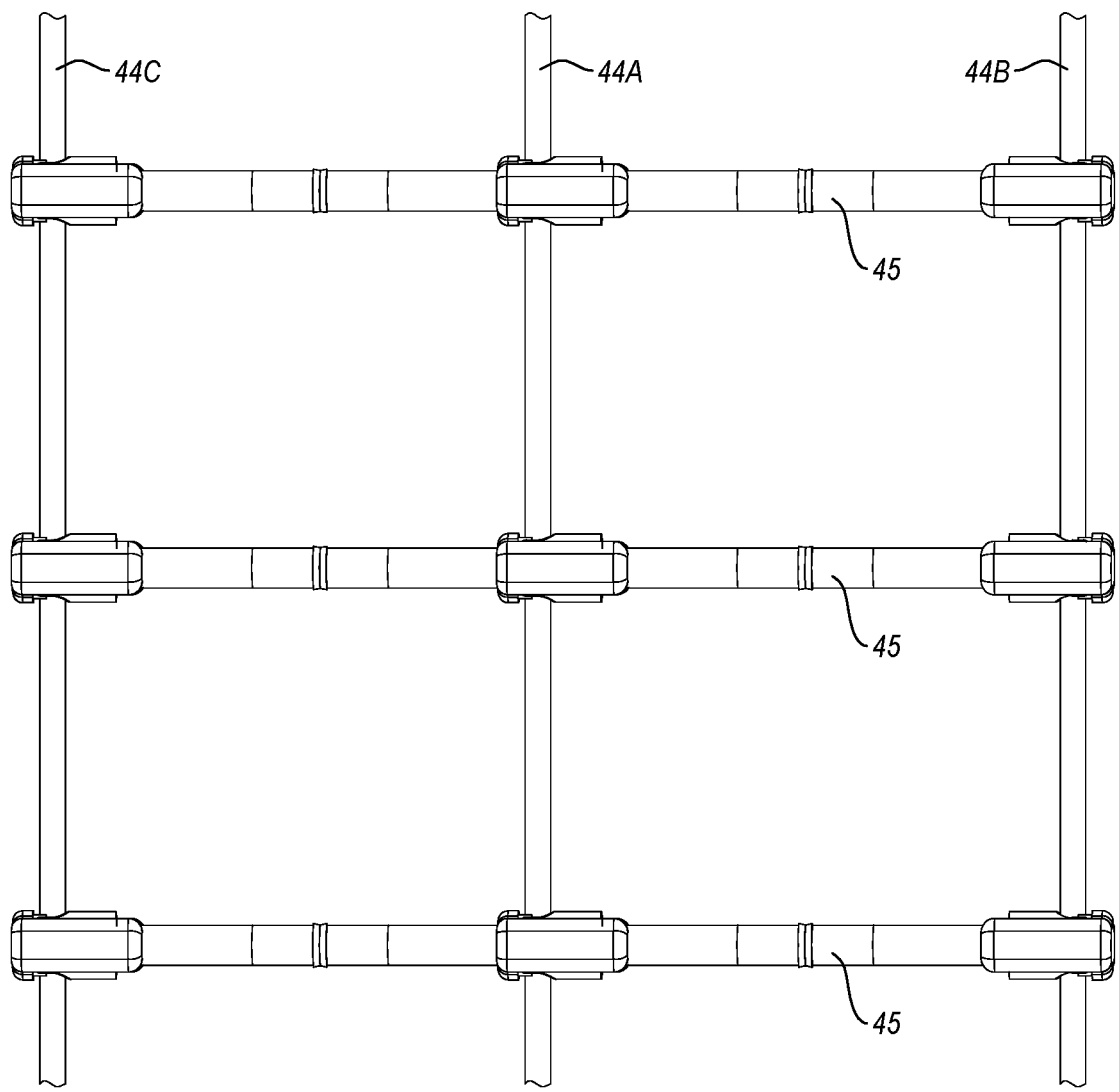
FIG. 14 is an elevated side view of a portion of an alternative embodiment of a mixing assembly having three laterally displaced drive lines.

In the above discussed embodiments, the mixing assemblies include two spaced apart drive lines 44A and 44B. In one alternative embodiment, depicted in FIG. 14, a mixing assembly can be formed having three laterally spaced apart drive lines 44A-C that extend between rotational assemblies 42A and B (FIG. 2). In a vertically extending resting state, all three drive lines 44A-C can be disposed within a single plane and disposed in substantially parallel alignment. A single continuous tie can extend between all three drive lines 44A-C at spaced apart positions along the length of drive lines 44A-C or one set of ties 45 can be used to separate drive lines 44A and 44B while a different set of ties 45 can be used to separate drive lines 44A and 44C.

Figure 15:
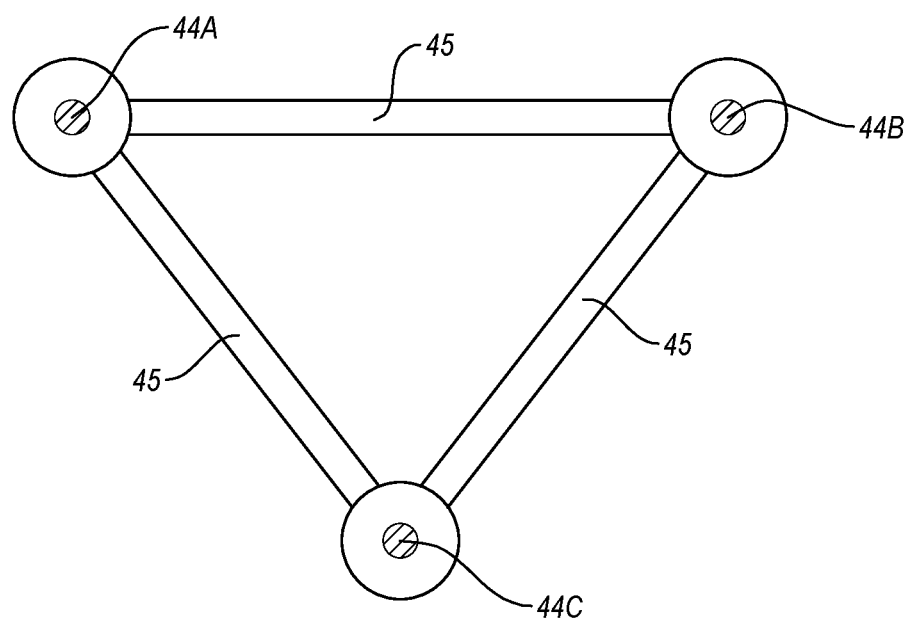
FIG. 15 is a cross sectional top plan view of an alternative embodiment of a mixing assembly having three drive lines in a triangular configuration.
Figure 16:
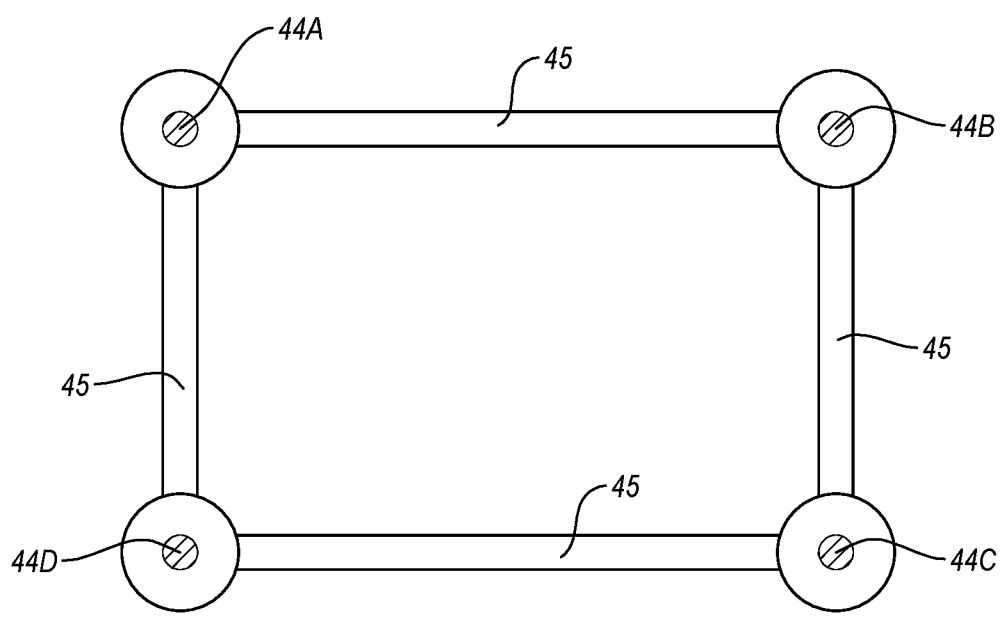
FIG. 16 is a cross sectional top plan view of an alternative embodiment of a mixing assembly having four drive lines in a rectangular configuration.

In another embodiment as depicted in FIG. 15, spaced apart drive lines 44A-C need not be disposed within a single plane but can be laterally spaced apart in a triangular configuration where again drive lines 44A-C can extend between rotational assemblies 42A and B (FIG. 2). In yet another embodiment, a mixing assembly can be formed having four laterally spaced apart drive lines 44A-D that extend between rotational assemblies 42A and B (FIG. 2). Drive lines 44A-D can be disposed in a square or rectangular configuration. In still other embodiments, mixing assemblies can be formed using other numbers of laterally spaced apart drive lines 44 such as 5, 6, 7, 8, 9 or more that can be disposed in a circular, polygonal, irregular or other configurations.

Figure 17:
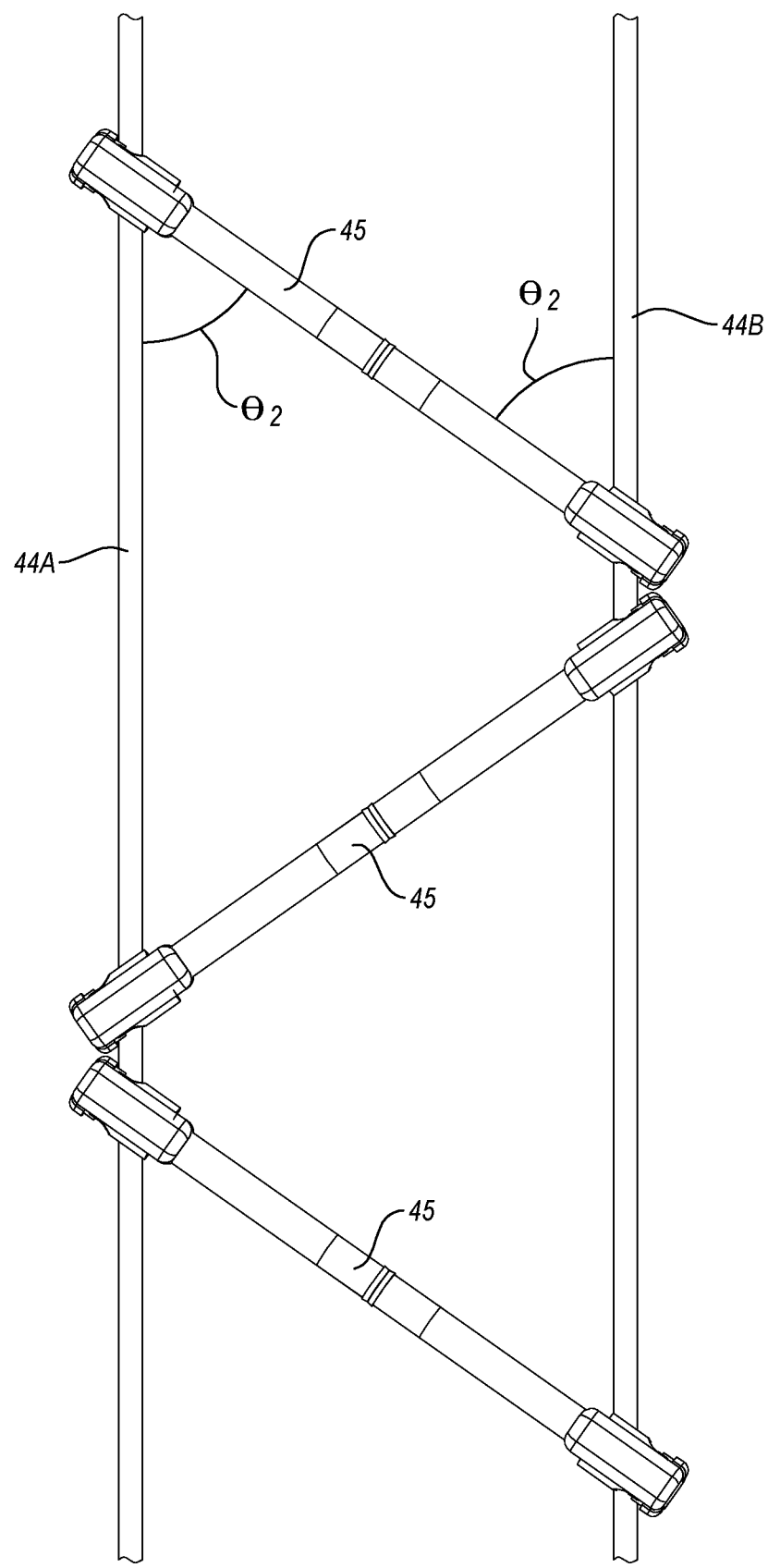
FIG. 17 is an elevated side view of a portion of an alternative embodiment of a mixing assembly having ties extending between laterally displaced drive lines at an acute angle.
Figure 18:
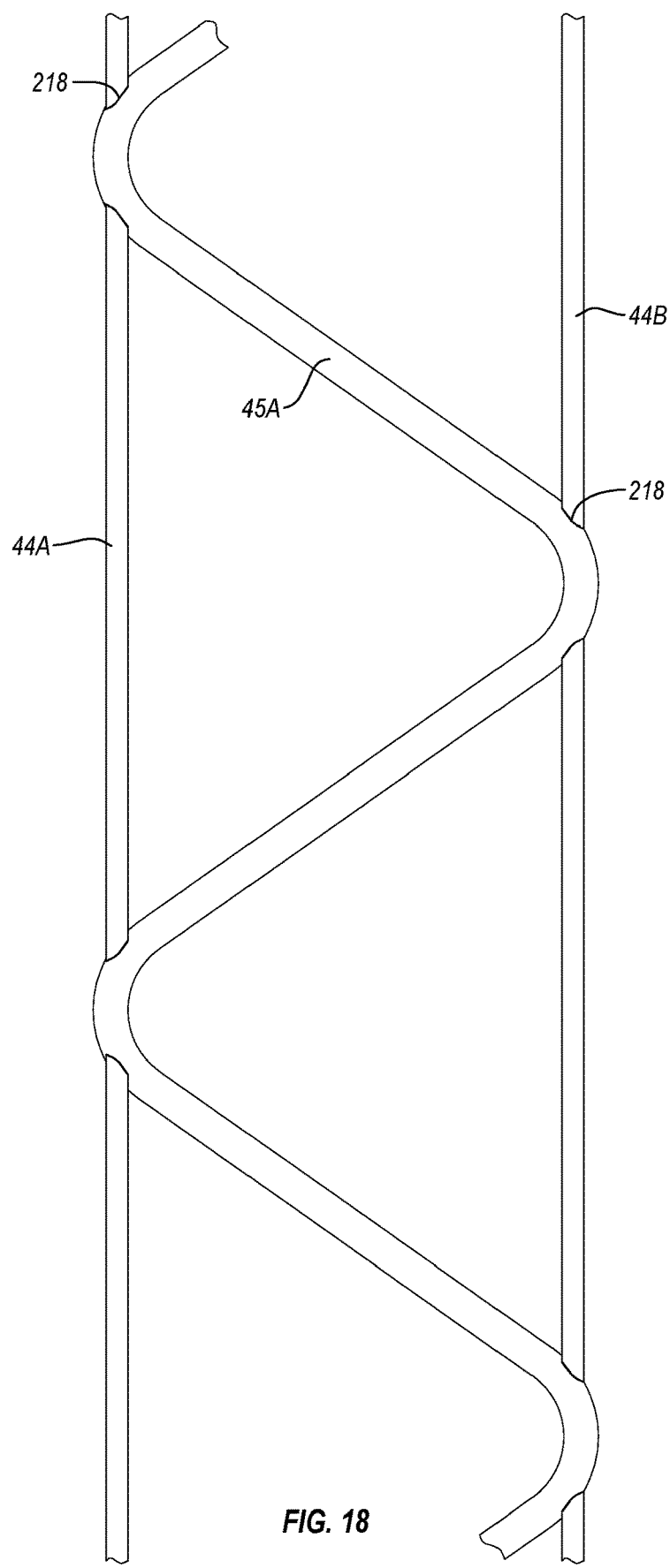
FIG. 18 is an elevated side view of a portion of an alternative embodiment of a mixing assembly having a single continuous tie extending along the length of two laterally disposed drive lines.

The above discussed mixing assemblies also depict ties 45 projecting normal or at right angles between drive lines 44. That is, ties 45 are disposed perpendicular to drive lines 44 when drive lines are vertically disposed. In alternative embodiments, however, ties 45 need not extend perpendicular to drive lines 44 but can project at an acute inside angle θ2 from each drive line 44A and B as depicted in FIG. 17. For example, the acute angle θ2 can be greater than, less than, or equal to 80°, 70°, 60°, 50°, 40°, 30°, or 20° or in a range between any two of the angles. In some embodiments, ties 45 extending between drive lines 44 need not be straight but can have a variety of different configurations such as circular, X-shaped, U-shaped, V-shaped, curved, arced, or the like. Furthermore, in contrast to having a plurality of separate ties that are used to hold drive lines 44, it is appreciated that one single continuous tie can extend along the length of drive lines 44 for holding spaced apart. For example, depicted in FIG. 18 is a single, continuous tie 45A that curves back and forth between drive lines 44A and B at spaced apart locations along the length of drive lines 44A and B. Openings 218 extend through tie 45A at the curved sections through which drive lines 44A and B can pass during assembly. Drive lines can then be freely movable within openings 218 or secured therein such as by crimping, adhesive, welding, fastener, press fit connection or the like.

Figure 19:
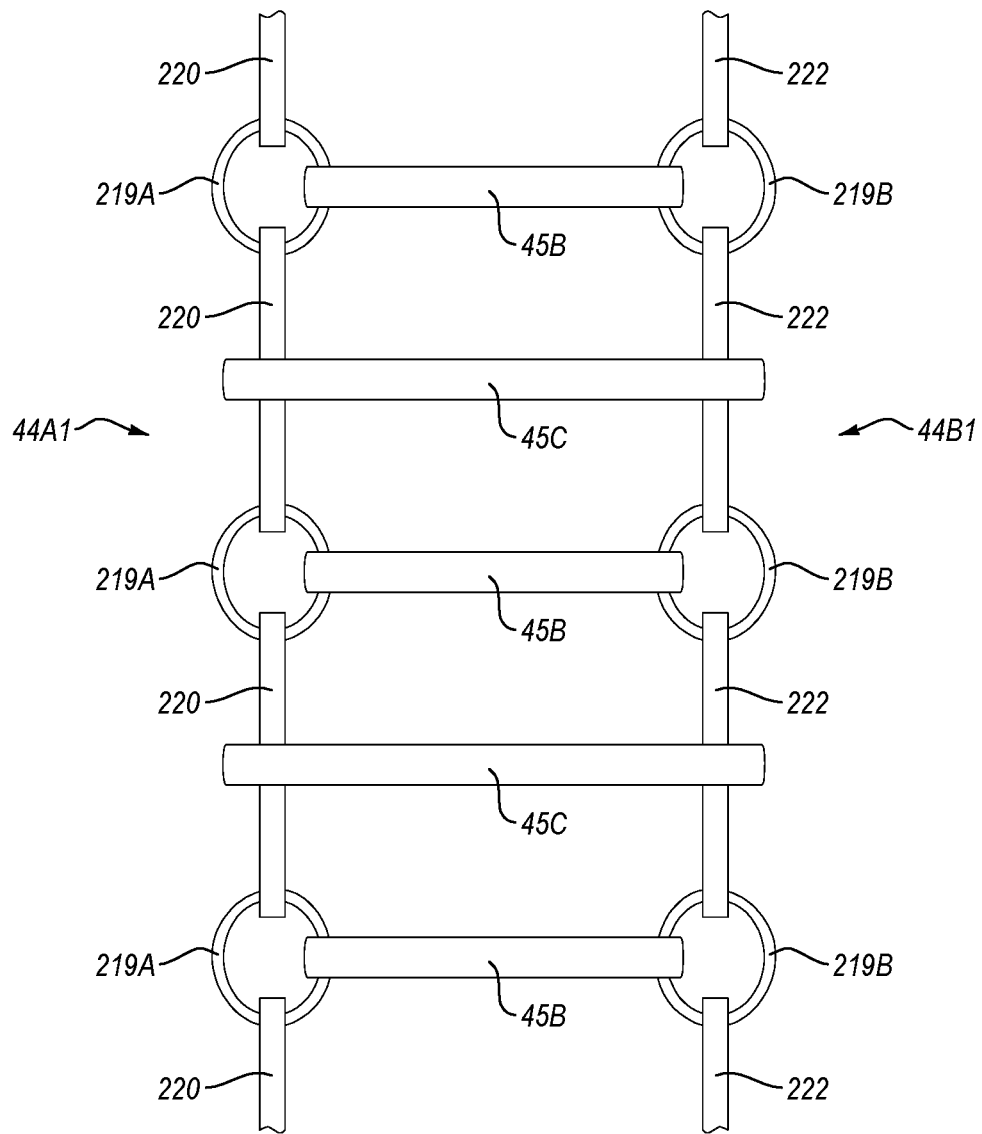
FIG. 19 is an elevated front view of a portion of an alternative embodiment of a mixing assembly having two drive lines formed from linked portions that are separated by ties.

In still other embodiments, each drive line 44 can comprise a separate continuous drive line (such as depicted in FIG. 3) or each drive line 44 can comprise a plurality of separate drive line sections that are coupled together. For example, as depicted in FIG. 19, a drive line 44A1 is depicted as comprising a plurality of separate drive line sections 220 that are hingedly connected in series by a plurality of connectors 219A. In this embodiment, connectors 219A are depicted as rings. In other embodiments, however, connectors 219A could come in a variety of different configurations such as crimps, hinges, balls, clamps, hooks, unions, or the like, which either rigidly or hingedly connect opposing ends of drive line sections 220 together. Where drive lines sections 220 are rigidly connected together, drive line sections 220 are typically made of a flexible material such as that previously discussed with regard to drive lines 44A and B. However, where drive line sections 220 are relatively short in length and are hingedly connected together, drive line sections 220 can be rigid or flexible. That is, even if drive line sections 220 are rigid, because the sections 220 are hingedly coupled together, the overall drive line 44A1 is flexible.

A drive line 44B1 is also depicted as comprising a plurality of separate drive line sections 222 that are hingedly connected in series by a plurality of connectors 219B. Connectors 219B can be the same configuration and alternatives as discussed with connectors 219A. A plurality of spaced apart ties 45B extend between drive lines 44A1 and 44B1 at spaced apart locations along the length of drive lines 44A1 and 44B1. Ties 45B extend between connectors 219A and 219B and can be either rigidly or hingedly connected thereto. In an alternative embodiment, ties 45B could be replaced with ties 45C that extend directly between laterally spaced apart adjacent drive line sections 220 and 222 and are either hingedly or rigidly connected thereto.

Figure 20:
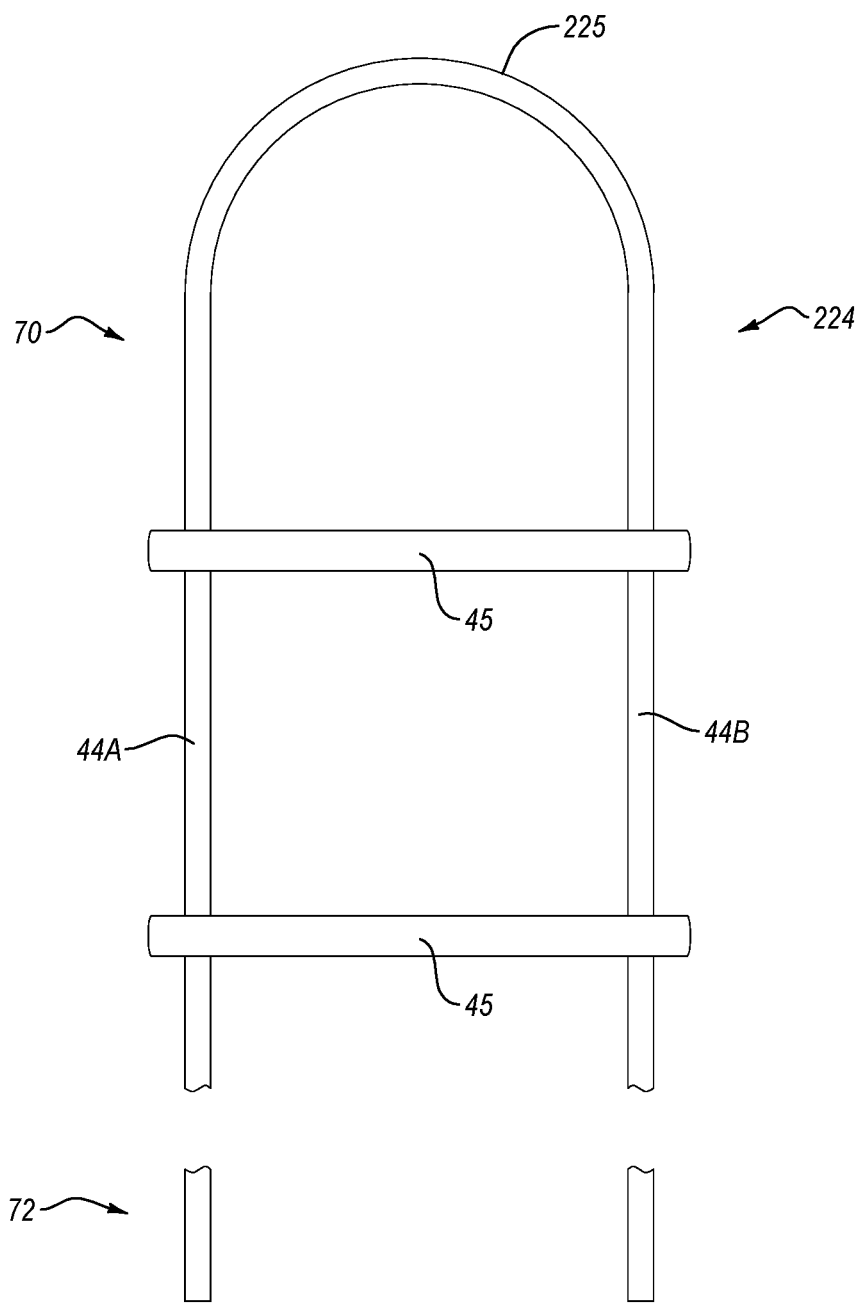
FIG. 20 is an elevated front view of a portion of an alternative embodiment of a mixing assembly having two drive lines that form part of one continuous line.

In yet another alternative embodiment, it is appreciated that drive lines 44A and B could be integrally formed as one continuous line. For example, as depicted in FIG. 20, a continuous line 224 is depicted that comprises drive line 44A and drive line 44B that both extend between first end 70 and opposing second end 72. Line 224, however, also includes a transition portion 225 that extends between first end 70 of drive lines 44A and 44B. As such, drive line 44A, drive line 44B and transition portion 225 combine to form a single, continuous, unitary line, i.e., line 224. First ends 70 of lines 44 can still be connected to rotational assembly 42A such as by using one of the above described mounts or methods. Second ends 72 of lines 44 can remain separate and discrete and connected to rotational assembly 42B as discussed above. In another alternative, second ends 72 of lines can be connected together by transition portion 225 while first ends 70 remain separate and discrete. In still another embodiment, drive lines 44A and B can be part of a continuous loop.

Figure 21A:
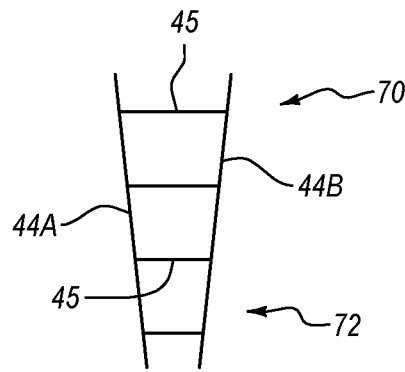
FIGS. 21A-21D are elevated front views of portions of alternative embodiments of mixing assemblies having two drive lines that are disposed in non-parallel configurations.
Figure 21B:
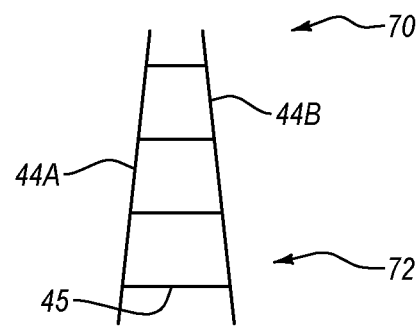
Figure 21C:
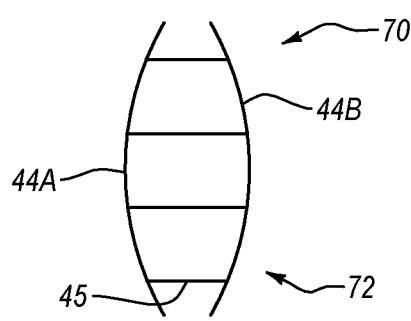
Figure 21D:
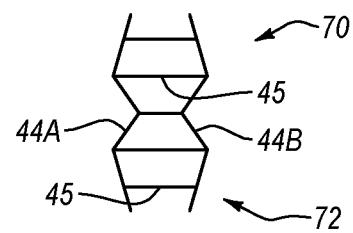

In the above discussed embodiments, drive lines 44 are shown as being disposed in substantially parallel alignment when in an extended, relaxed, untwisted state. However, in alternative embodiments drive lines 44 need not be disposed in parallel alignment when in a relaxed state. For example, in the embodiment in FIG. 21A, drive lines 44 converge towards each other as they extend from first end 70 to second end 72 but are maintained laterally spaced apart by ties 45 extending therebetween. In the embodiment in FIG. 21B, drive lines 44 diverge away from each other as they extend from first end 70 to second end 72. In the embodiment depicted in FIG. 21C, drive lines 44 outwardly curve in symmetrical arcs as they extend from first end 70 to second end 72. In the embodiment depicted in FIG. 21D, drive lines 44 extend in a changing pattern, such as a zigzag pattern, as they extend from first end 70 to second end 72. In still other embodiments, drive lines 44 can extend in other non-parallel patterns that are symmetrical, non-symmetrical, repeating or non-repeating.

Figure 22:
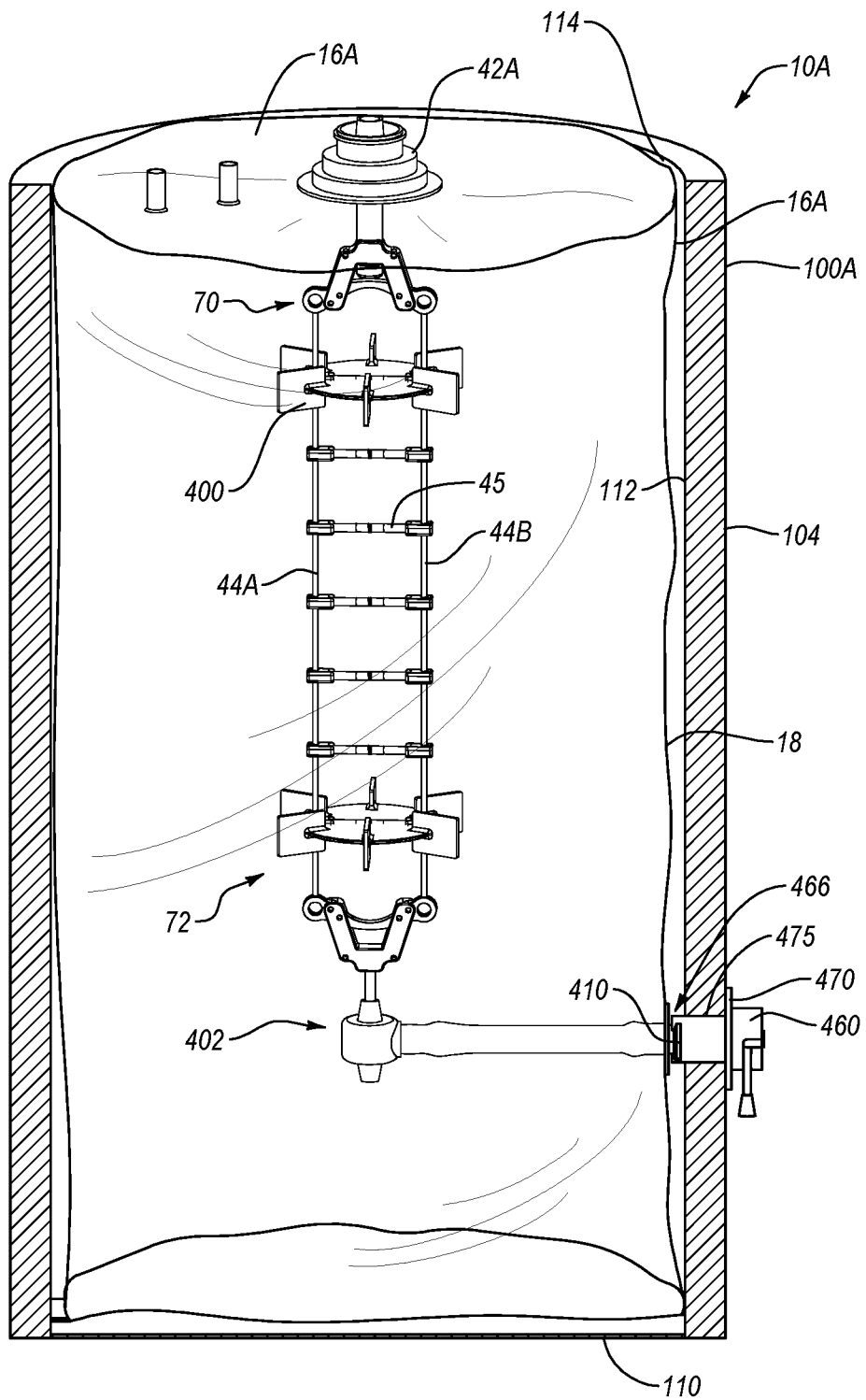
FIG. 22 is a partial cross sectional front view of an alternative embodiment of a fluid mixing system that includes a container assembly with a lateral support assembly and a support housing.

In the prior discussed embodiments incorporating the flexible drive lines, the flexible drive lines are supported by being secured to both the upper end wall and lower end wall of container 18. In an alternative embodiment, the flexible drive lines can be supported and stabilized by being secured to the upper end wall of the container and at one or more locations along the length of the flexible drive lines. For example, depicted in FIG. 22 is an alternative embodiment of a fluid mixing system 10A incorporating features of the present invention. Fluid mixing system 10A comprises a container assembly 16A at least partially disposed within the compartment of a support housing 100A. Like elements between container assembly 16 and 16A and between support housing 100 and 100A are identified by like reference characters. Furthermore, disclosure and alternative embodiments as previously discussed with regard to container 16 and support housing 100 are also applicable to corresponding elements of container assembly 16A and support housing 100A.

Figure 23:
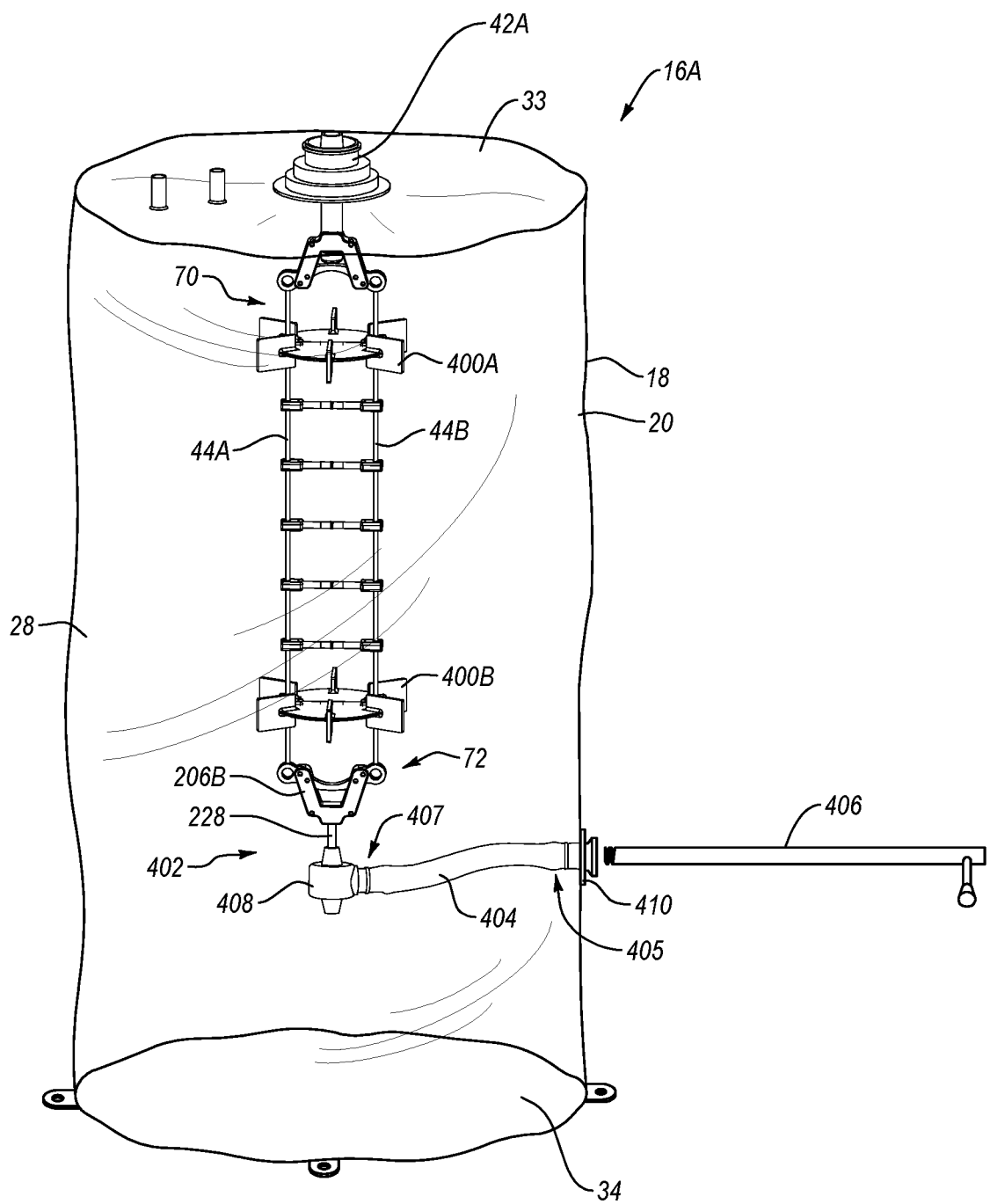
FIG. 23 is a partially exploded front view of the container assembly shown in FIG. 22.

As depicted in FIG. 23, container assembly 16A comprises container 18 having flexible drive lines 44A and B disposed therein. First end 70 of flexible drive lines 44 are secured to upper end wall 33 of container 18 by rotational assembly 42A. Mounted on flexible drive lines 44 as spaced apart locations are mixing elements 400A and B. Each of mixing element 400A and B can comprise an impeller or other types of mixing elements. In alternative embodiments, container assembly 16A can comprise one, three, or four or more mixing elements 400. In contrast to container assembly 16 where second end 72 of drive lines 44 are secured to lower end wall 34, container assembly 16A has second end 72 of drive lines 44 suspended above lower end wall 34 and not connected thereto.

To stabilize drive lines 44 within compartment 28 of container 18, container assembly 16A comprises a lateral support assembly 402. As discussed below in more detail, a hub 228 is rotatably mounted to lateral support assembly 402 while mount 206B secures second end 72 of drive lines 44 to hub 228. Lateral support assembly 402 comprises a retention assembly 404 having a first end 405 secured to side 20 of container 18 and an opposing second end 407 secured to hub 228. Lateral support assembly 402 also includes a support rod 406 that is selectively received and secured within retention assembly 404. Retention assembly 404 comprises a port fitting 410 at first end 405 that is coupled with side 20 of container 18, a receiver 408 at second end 407 to which hub 228 is rotatably mounted, and a flexible tube 412 that extends between port fitting 410 and receiver 408.

Figure 24:
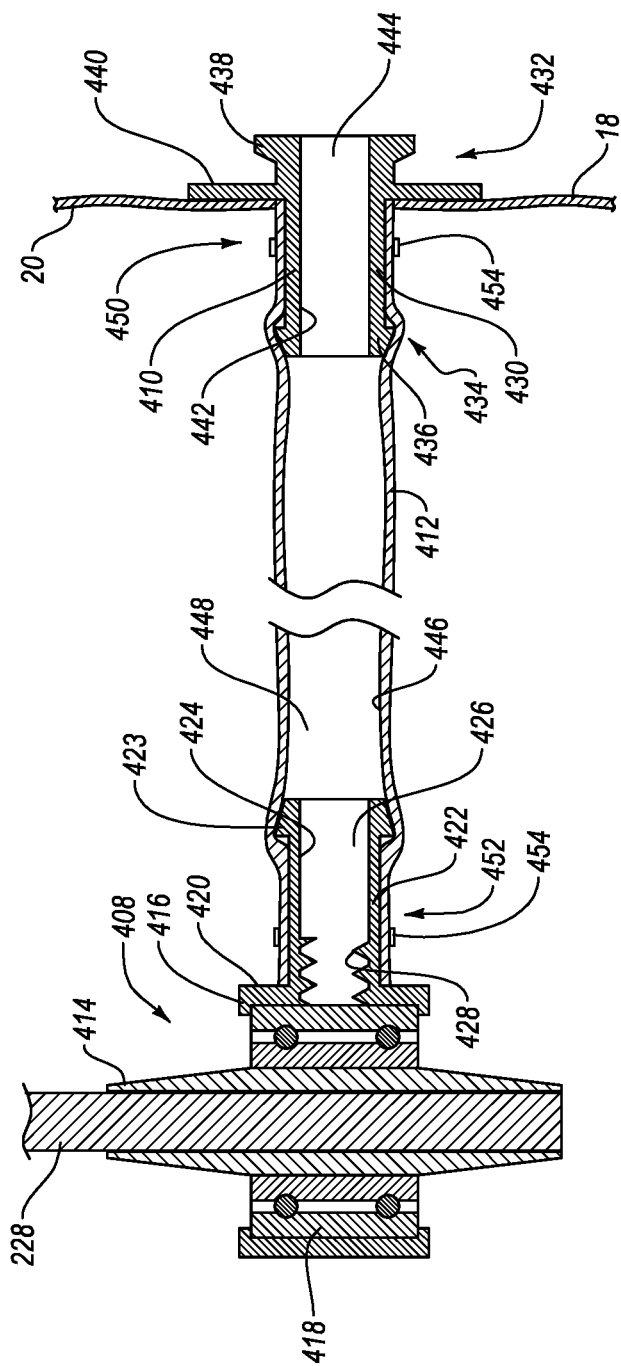
FIG. 24 is a cross sectional side view of a retention assembly which forms a portion of the lateral support assembly shown in FIG. 22.

As depicted in FIG. 24, receiver 408 comprises an inner housing 414 that is securely fixed to hub 228 such as by crimping, adhesive, clamps, fasteners, or the like. Receiver 408 also includes an outer housing 416 that encircles inner housing 414. A bearing 418, such as a ball thrust bearing, roller thrust bearing, or other type of bearing, is disposed between inner housing 414 and outer housing 416. Bearing 418 enables inner housing 414 and hub 228 to rotate concurrently relative to outer housing 416. Outer housing 416 includes a body 420 having a tubular stem 422 outwardly projecting therefrom. Stem 422 can be integrally formed with or secured to body 420. An annular barb 423 can encircle and outwardly project on the end of stem 422 for engaging with flexible tube 412. Stem 422 has an interior surface 424 that bounds an opening 426 that can extend into body 420. Formed on interior surface 424 of stem 422 and/or body 420 is an engaging thread 428.

As also depicted in FIG. 24, port fitting 410 comprises a tubular stem 430 having a first end 432 and an opposing second end 434. An annular barb 436 can encircle and outwardly extending from second end 434 for engaging with flexible tube 412. Radially outwardly projecting from first end 432 is a retention flange 438. As will be discussed below in greater detail, retention flange 438 is used to secure port fitting 410 to rigid support housing 100. Retention flange 438 need not encircle stem 430 and can have a variety of different configurations. Encircling and radially outwardly projecting from stem 430 at a location between opposing ends 432 and 434 is a mounting flange 440. Mounting flange 440 is welded or otherwise secured to side 20 of container 18 so as to form a liquid tight seal therewith. As a result, first end 432 of port fitting 410 disposed outside of container 18 while second end 434 is disposed within container 18. Stem 430 has an interior surface 442 that bounds a passageway 444 extending therethrough.

Flexible tube 412 can comprise any type of flexible tube, tubing, hose, pipe or the like and is typically comprised of an elastomeric polymer. By making tube 412 flexible, tube 412 can be folded or rolled when collapsing container 18 for shipping, storage, disposal or the like. In an alternative embodiment it is appreciated that tube 412 need not be flexible but can be rigid or semi-rigid. Tube 412 has an interior surface 446 that bounds a passageway 448 that longitudinally extends through tube 412 from a first end 450 to an opposing second end 452. First end 450 of tube 412 is advanced over stem 430 of port fitting 410 so as to form a liquid tight seal therewith while second end 452 of tube 412 is received over stem 422 of receiver 408 so as to form a liquid type seal therewith. A fastener 454 such as a pull tie, crimp, clamp, or similar structure can be secured around first end 450 and second end 452 so as to secure the engagement between tube 412 and stems 422 and 430.

Figure 25:
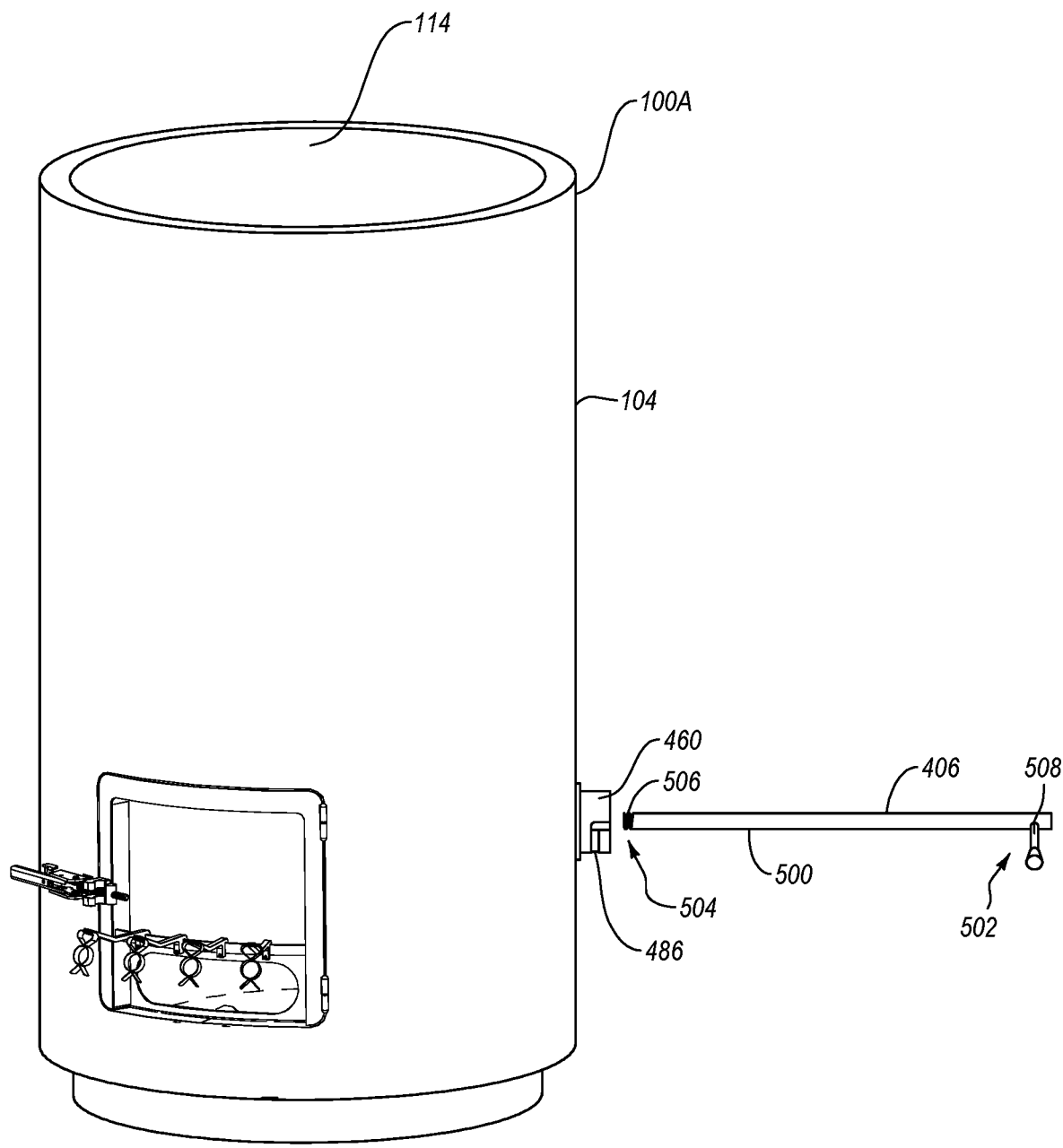
FIG. 25 is a perspective view of the support housing shown in FIG. 22 with the support rod exploded therefrom.
Figure 26:
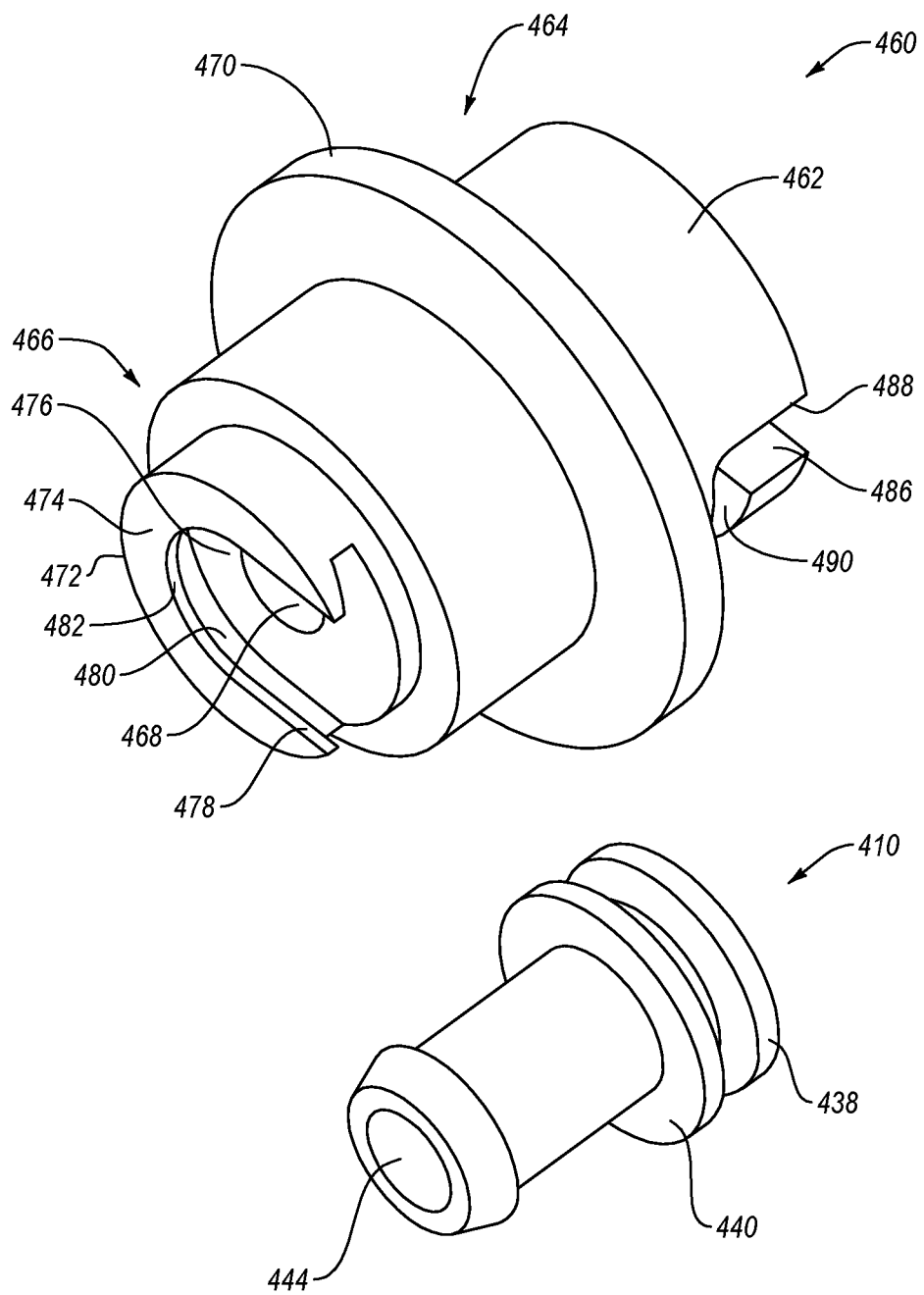
FIG. 26 is a perspective view of a locking insert that is disposed on the side of the support housing shown in FIG. 25.

During use, as depicted in FIG. 22, container assembly 16A is received within chamber 114 of support housing 100A. Support housing 100A is substantially identical is support housing 100 as previously discussed with regard to FIG. 1 and like elements are identified by like reference characters. Support housing 100A is distinguished from support housing 100 in that it does not include retainer 140 located on floor 110 (FIG. 1). Rather, support housing 100A includes a locking fitting 460 mounted on sidewall 104. As depicted in FIGS. 25 and 26, locking fitting 460 comprises a base 462 having a first end 464 and an opposing second end 466. A passageway 468 centrally passes through base 462 between opposing ends 464 and 466. A flange 470 can encircle and radially outwardly project from base 462 at a location between opposing ends 464 and 466. During the manufacture of support housing 100A, a hole 475 (FIG. 22) can be formed through sidewall 104 so as to extend to chamber 114. Second end 466 of each locking fitting 460 is received within hole 475 so that flange 470 hits against the exterior surface of sidewall 104. Welding or other fastening techniques can then be used to secure each locking fitting 460 to support housing 100A within the corresponding hole 475.

With reference to FIG. 26, formed on the end face of base 462 at second end 466 is a catch 472. Catch 472 is disposed adjacent to interior surface 112 of support housing 100A and has a U-shaped body 474 with a U-shaped opening 476 passing therethrough. U-shaped opening 476 is aligned with passageway 468 passing through base 462. Body 474 has an interior surface 478 that includes an undercut U-shaped channel 480 and a U-shaped catch lip 482 that radially inwardly projects adjacent to channel 480. Catch 472 is configured so that retention flange 438 on port fitting 410 can be slidably received and captured within channel 480 so that passageway 468 of locking fitting 460 is aligned with passageway 444 of port fitting 410. It is appreciated that retention flange 438 and/or channel 480 can be tapered so that a releasable friction fit is formed therebetween. It is also appreciated that there are a variety of different fastening techniques that can be used to releasably secure port fitting 410 to locking fitting 460.

Locking fitting 460 also includes a locking slot 486 formed on first end 464 of base 462 and which is located outside of support housing 100A. Locking slot 486 includes a first leg 488 that passes through base 462 to passageway 468 and runs parallel to passageway 468. Locking slot 486 also includes a second leg 490 that extends normal to first leg 488 at the end thereof so as to extend around a portion of the perimeter of base 462. Second leg 490 also extends to passageway 468.

Returning to FIG. 25, each support rod 406 comprises a linear shaft 500 that extends between a first end 502 and an opposing second end 504. A locking thread 506 is formed on second end 504. A locking arm 508 radially outwardly projects from shaft 500 at first end 502. Locking arm 508 is sized to be received within locking slot 486. Support rod 406 is typically comprised of metal but other rigid or semi-rigid materials can also be used.

Figure 27:
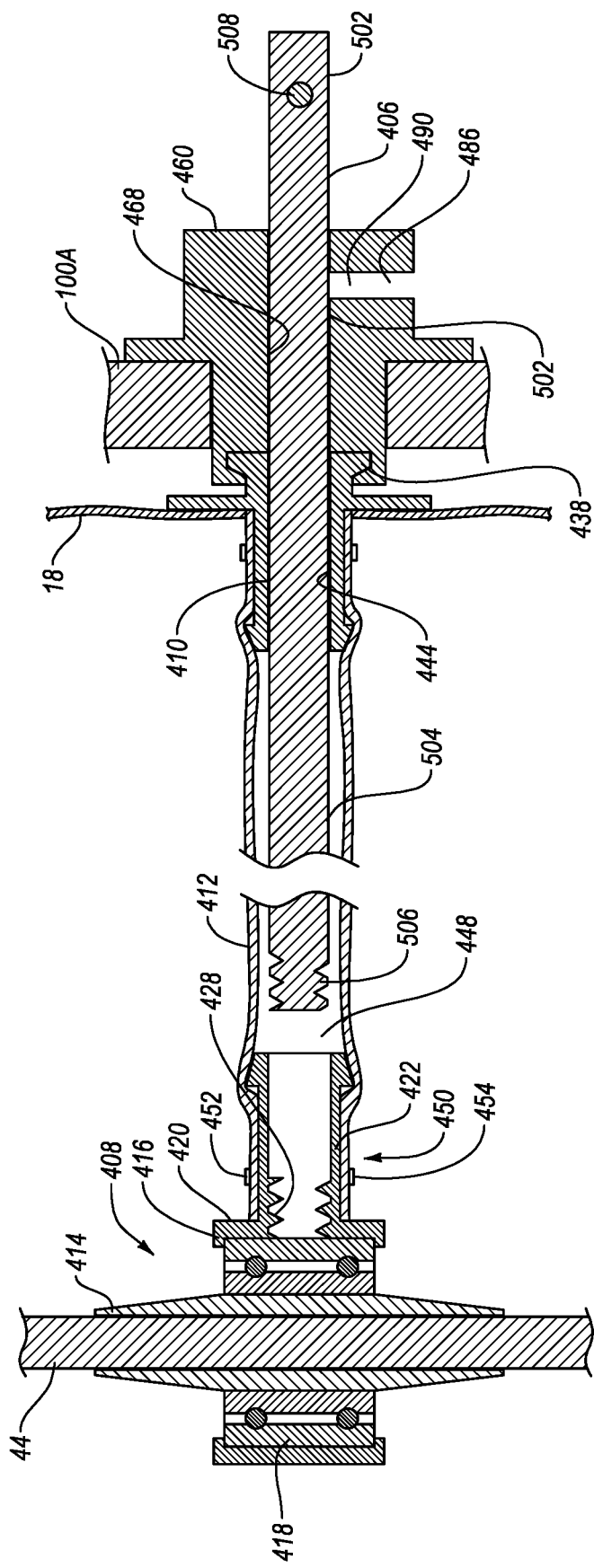
FIG. 27 is a cross sectional side view of the retention assembly having the support rod partially inserted therein.
Figure 28:
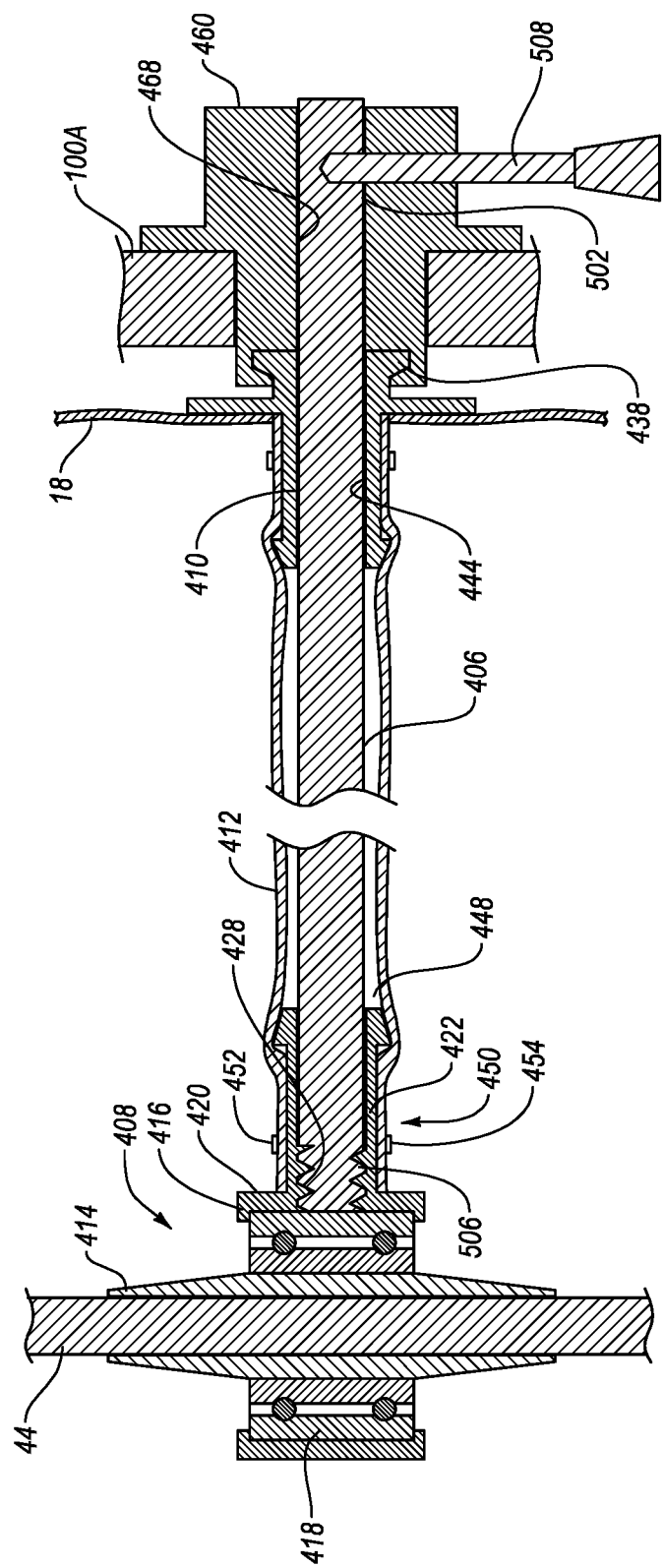
FIG. 28 is a cross sectional side view of the retention assembly having the support rod fully inserted and locked therein.

During use, as previously discussed and depicted in FIG. 22, container assembly 16A is received within chamber 114 of support housing 100A. Once inserted, each port fitting 410 is secured to a corresponding locking fitting 460 as previously discussed and depicted in FIG. 27. In this assembled configuration, second end 504 of support rod 406 is advanced through passageway 468 of locking fitting 460 through passageway 444 of port fitting 410 and into passageway 448 of tube 412. Each support rod 406 is continued to be advanced until locking thread 506 reach engaging thread 428 on retention assembly 404. Concurrently, locking arm 508 is received within first leg 488 (FIG. 26) of locking slot 486. In this position, locking arm 508 can be rotated downward through second leg 490 of locking slot 486 so as to lock support rod 406 to locking fitting 460. As locking arm 508 is rotated, shaft 500 with locking threads 506 thereon are rotated. As locking threads 506 are rotated they threadedly engage with engaging threads 428 on receiver 408, thereby securing support rod 406 to receiver 408. As a result, opposing ends of support rod 406 are secured to locking fitting 460 and receiver 408 which creates both a vertical and lateral rigid support for hub 228 and thus also creates a vertical and lateral rigid support for flexible drive lines 44. It is appreciated that a variety of other connections can be used for securing one or both of opposing ends of support rod 406 such as a bayonet connection, luer-lock connection, clamp, separate fastener, or the like.

The vertical and lateral rigid support of flexible drive lines 44 by lateral support assembly 402 achieves a number of benefits. For example, where mixing element 400 is an impeller, the rotation of the impeller causes the impeller to tend to migrate laterally. Lateral movement of drive lines 44 and mixing elements 400 can cause damage to container 18 and can produce irregular mixing within container 18. Irregular mixing can be especially problematic where the mixing system is being used as a bioreactor or fermentor used for growing cells or microorganism. In those cases, irregular mixing can apply unwanted shear forces on the cells or microorganism or can result in irregular feeding or gas transfer to the cells or microorganism. Use of the lateral support assembly prevents unwanted lateral movement of drive line 44 and mixing elements 400 within container 18 and helps maintain uniform mixing. Although in the depicted embodiment only one lateral support assembly 402 is shown, in alternative embodiments, container assembly 16A can be formed with two, three or more vertically spaced part lateral support assemblies. That is, drive lines 44 could converge onto spaced apart hubs at different locations along the height of container 18. A separate lateral support assembly 402 could then be connected to each separate hub, thereby laterally supporting drive lines 44 at different locations.

As a result of the vertical and lateral support to drive lines 44, second end 72 of drive lines 44 need not be connected to lower end wall 34 of container 18. In some cases, this is beneficial because it permits a more convenient folding of container 18. That is, in some designs for container 18, the most compact folding of container 18 requires that the center of opposing end walls 33 and 34 be pulled away from each other. Where drive line 44 is secured to the opposing end walls 33 and 34, the end walls cannot be pulled away from each other and thus container 18 cannot be folded in the most compact manner.

Figure 29:
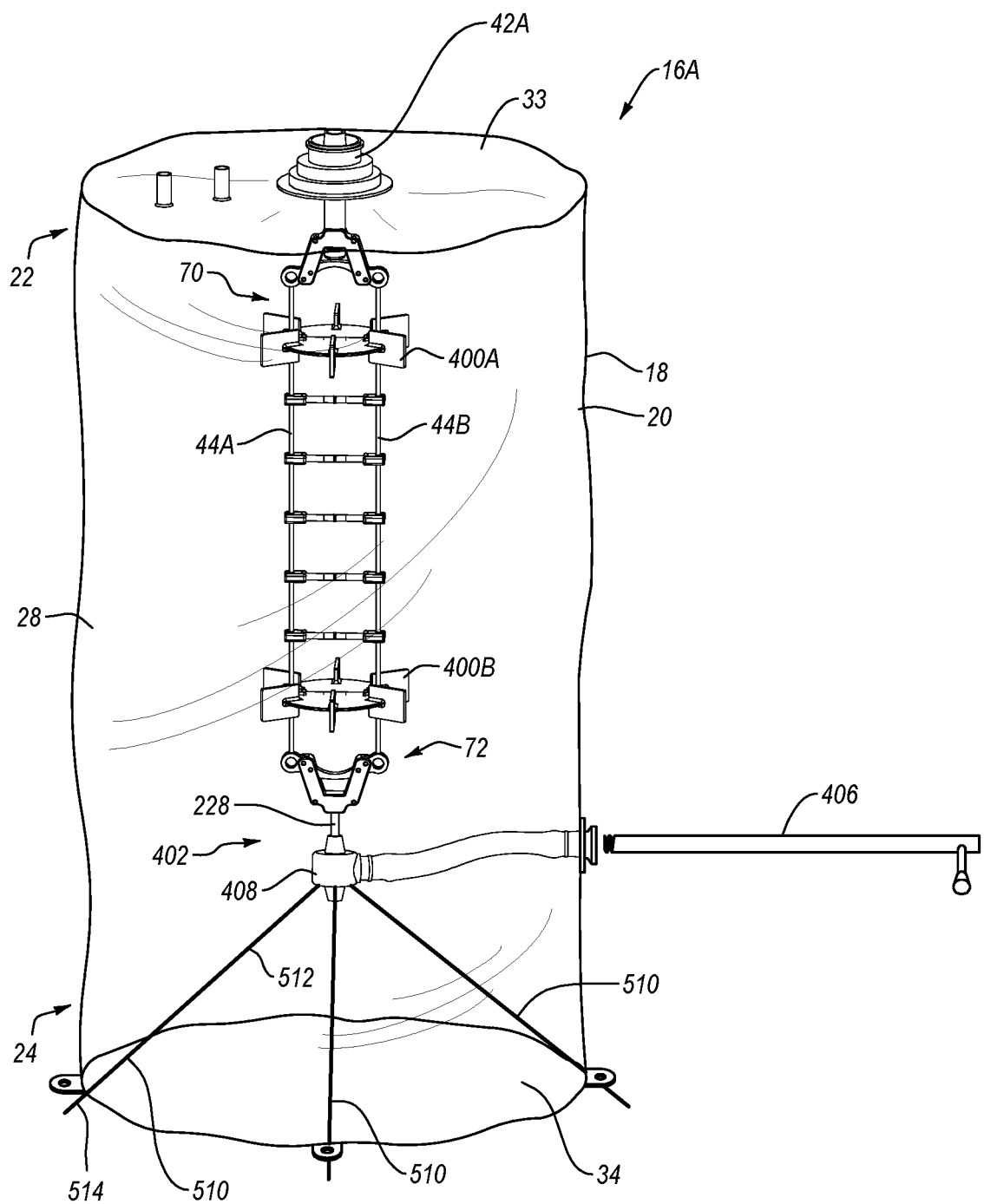
FIG. 29 is a cross sectional side view of an alternative container assembly further comprising guy-lines partially supporting the lateral support assembly.

As depicted in FIG. 29, if further lateral and/or vertical support is required for second ends 72 of drive lines 44, guy-lines 510 can be used to add the additional support. Specifically, a plurality of guy-lines 510 each have a first end 512 and an opposing second end 514. The first ends 512 can be connected to receiver 408 while the second ends 514 can pass through container 18 (in sealed engagement) at lower end 24 and be disposed outside of container 18. During use, when container 18 is disposed within support housing 100A (FIG. 25), guy-lines 510 can be tensioned and second ends 514 connected to support housing 100A or some other structure disposed outside of container 18. Guy-lines 510 can be made of the same materials and have the same properties as drive lines 44. Lines with other properties can also be used. Although three guy-lines 510 are shown in FIG. 29, in alternative embodiments, it is appreciated that 1, 2, 4, 5 or more guy-lines 510 can be used.

Figure 30:
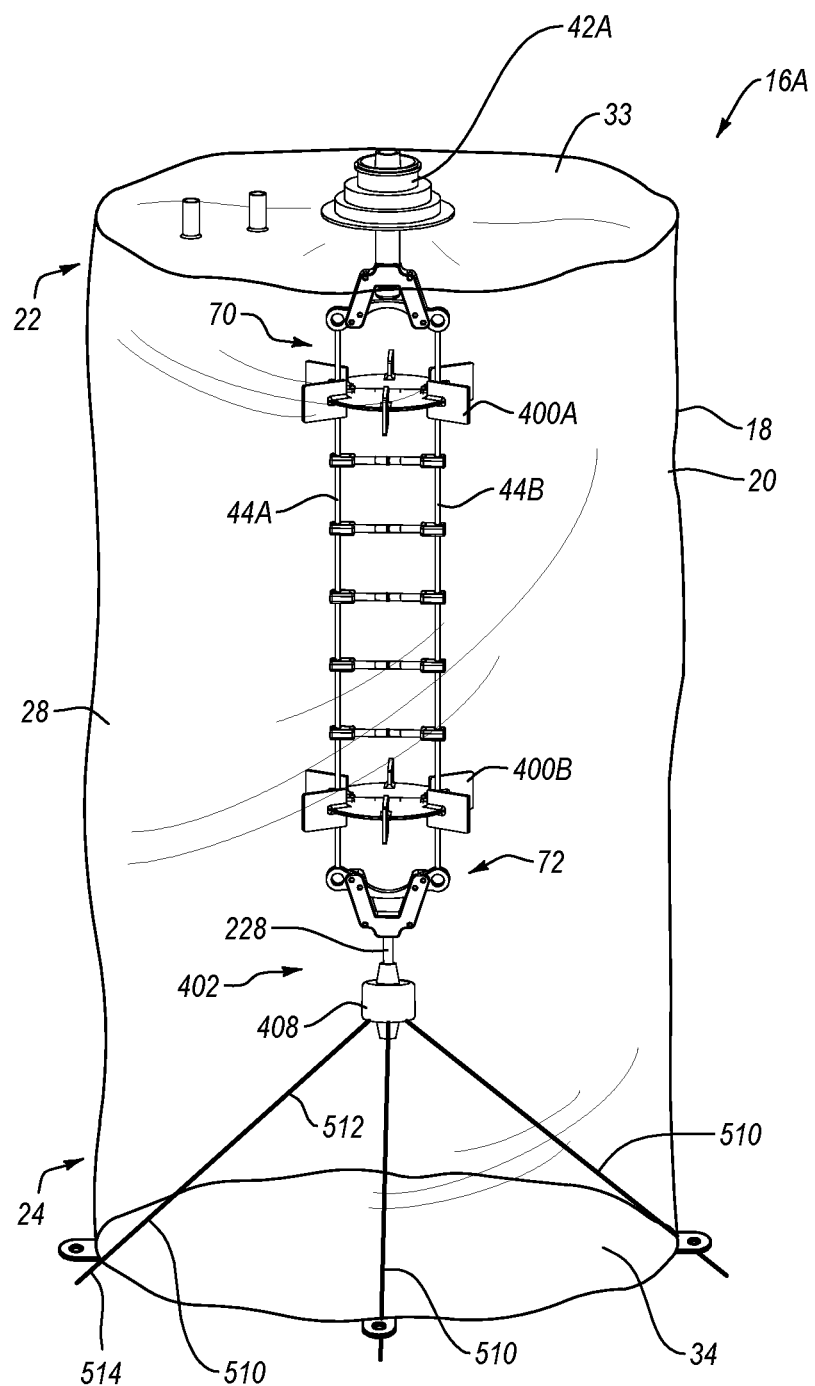
FIG. 30 is a cross sectional side view of an alternative container assembly wherein guy-lines independent support the lower end of the mixing assembly.

In a similar alternative embodiment depicted in FIG. 30, guy-lines 510 can be used to independently laterally and vertically support second end 72 of drive lines 44. Specifically, receiver 408 as previously discussed (without tubular stem 422) can be used to rotatably support hub 228. The plurality of radially spaced apart guy-lines 510 can again have first end 512 connected to receiver 408 and opposing second end 514 passing through container 18 and connecting to support housing 100 or some other structure outside of support housing 100. In contrast to the system depicted in FIG. 29, however, other than using receiver 408, the remainder of lateral support assembly 402 can be eliminated.

As in other embodiments, the above system can be inverted by having guy-lines 510 support first end 70 of drive lines 44 and while second end 72 of drive lines 44 are supported by second rotational assembly 42B as depicted in FIG. 2. Likewise, in another alternative to the embodiment depicted in FIG. 22, first rotational assembly 42A can be eliminated and first ends 70 of drive lines 44 can be laterally and vertically supported by positioning lateral support assembly 402 at first ends 70 of drive lines 44. Second rotational assembly 42B can then be used to secure second end 72 of drive lines 44 to lower end wall 34 of the container in the same manner as depicted and previously discussed with regard to FIG. 2.

Figure 31:
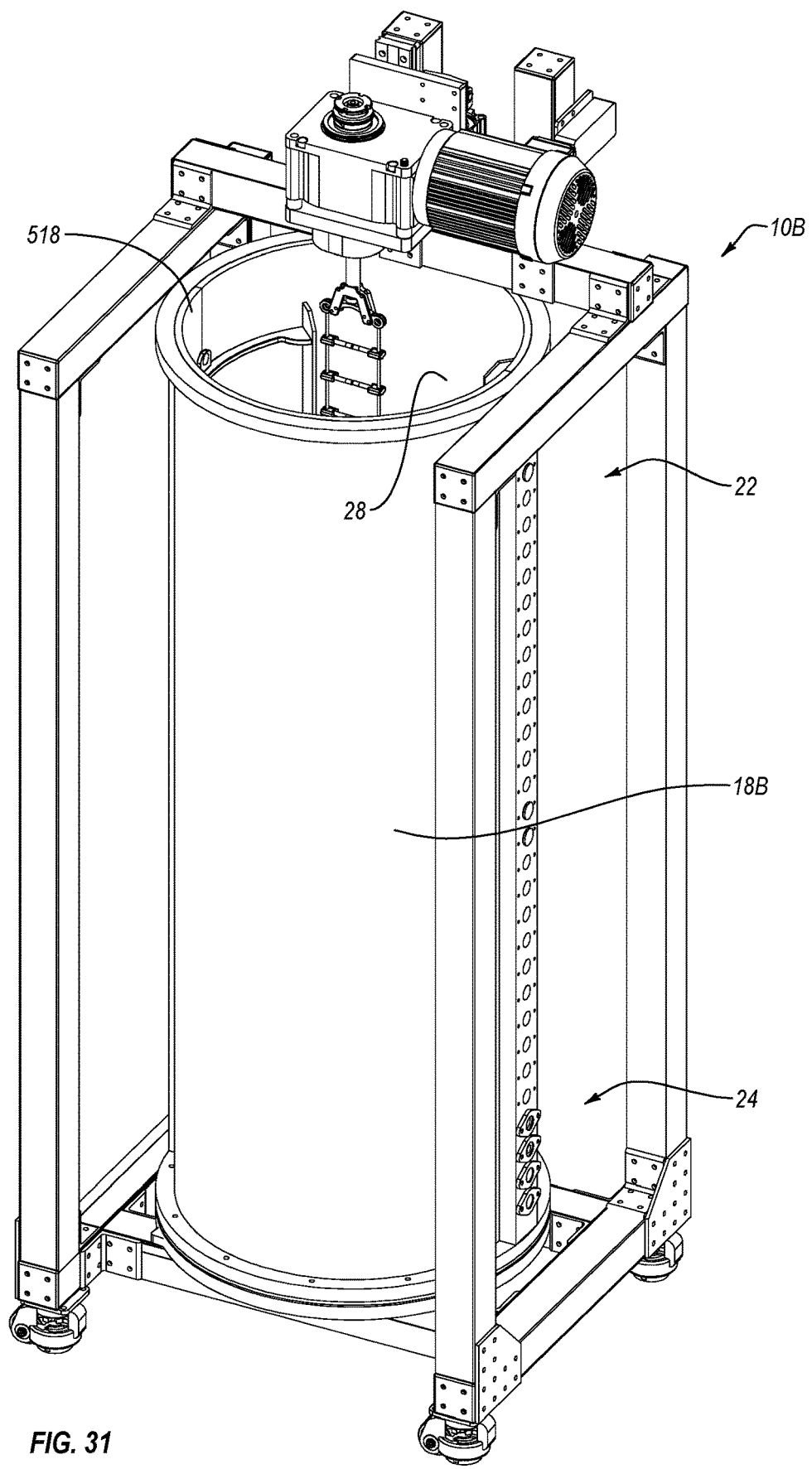
FIG. 31 is a perspective view of an alternative fluid mixing system wherein the mixing assembly shown in FIG. 2 is disposed within a rigid container.
Figure 32:
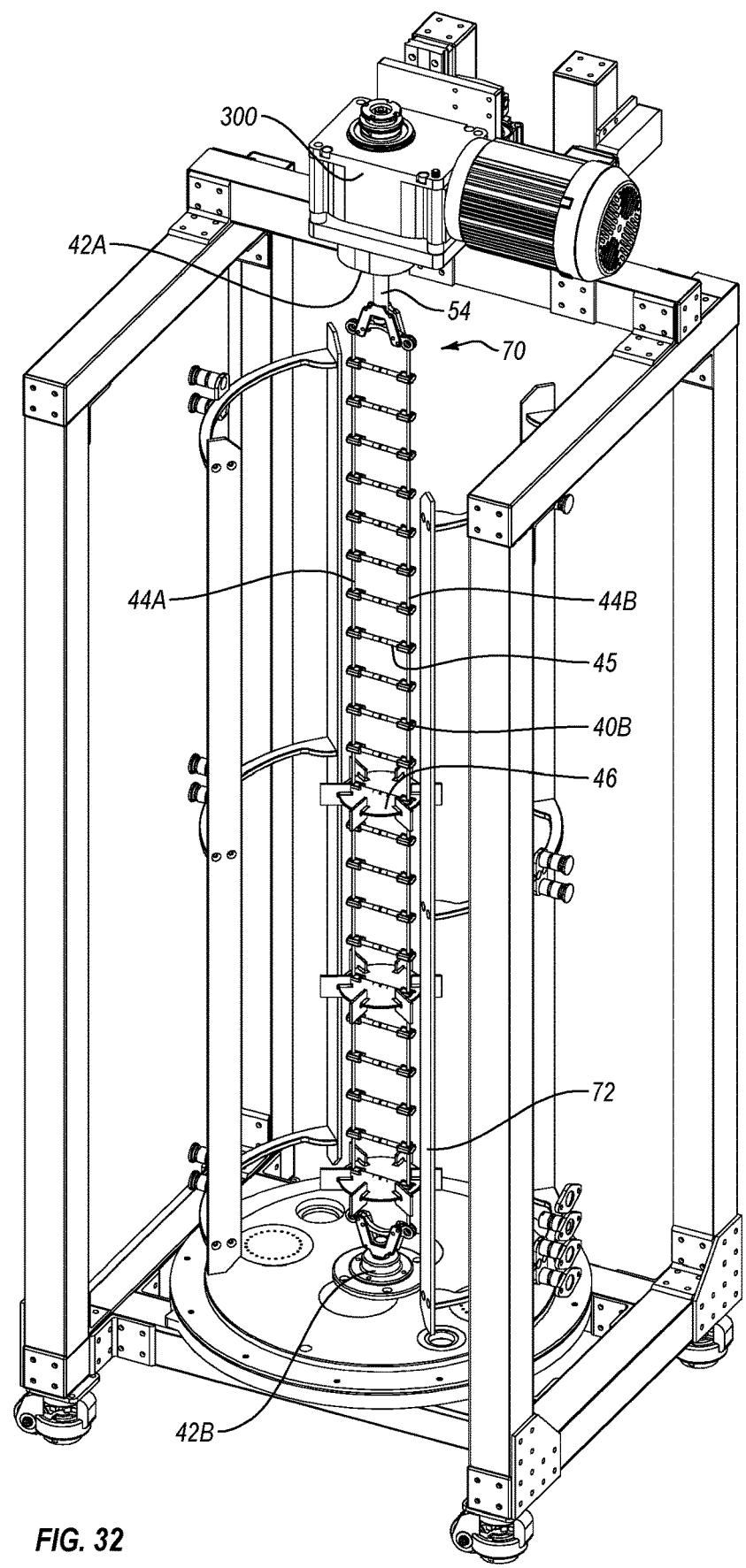
FIG. 32 a perspective view of the fluid mixing system shown in FIG. 31 with the sidewall of the rigid container removed.

In most of the above embodiments, container 18 is discussed and depicted as being a flexible bag. In alternative embodiments, however, the container can comprise a rigid container. For example, depicted in FIGS. 31 and 32 is a mixing system 10B. Like elements between mixing systems 10 and 10B are identified by like reference characters. Mixing system 10B comprises a container 18B having compartment 28. Container 18B, however, is rigid, such as by being made of a metal like stainless steel, and has an exposed opening 518 located at upper end 22. At least partially disposed within compartment 28 is a mixing assembly 40B that includes drives lines 44A and B, ties 45, and impeller 46 or other mixing elements as previously discussed. Rotational assembly 42A can be used to connect first end 70 of drive lines 44 to drive motor assembly 300. However, rotational assembly 42A does not directly connect to container 18B. The same process as discussed above can be used to rotate mixing assembly 40B within compartment 28 to mix the fluid therein. In this embodiment, however, compartment 28 is not sealed closed and thus is not sterile.

The present invention may be embodied in other specific forms without departing from its spirit or essential characteristics. For example, all of the features discussed above with regard to each of the different embodiments can be mixed and matched between the different embodiment to create new embodiments. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A bioreactor or fermentor system for culturing cells or microorganisms, the system comprising:

a container bounding a compartment, the compartment being configured for culturing cells or microorganisms, the container having a first end and an opposing second end;

an elongated first drive line disposed within the compartment of the container and having a length extending between a first end and an opposing second end, at least a portion of the length of the first drive line being flexible;

an elongated second drive line disposed within the compartment of the container and having a length extending between a first end and an opposing second end, at least a portion of the length of the second drive line being flexible, the first drive line and second drive line being rotatable within the compartment of the container;

at least one tie extending between the first drive line and the second drive line so as to maintain at least a portion of the first drive line and the second drive line at lateral spaced apart positions within the compartment, the at least one tie being more rigid than the first drive line and the second drive line; and wherein the first end of the first drive line and the second drive line are rotatably connected to the first end of the container and the second end of the first drive line and the second drive line are rotatably connected to the second end of the container.

2. The bioreactor or fermentor system as recited in claim 1, wherein the at least one tie comprises a plurality of spaced apart ties extending between the first drive line and the second drive line and being spaced apart along the length of the first drive line and the second drive line, the plurality of ties maintaining the at least a portion of the first drive line and the second drive line at lateral spaced apart positions.

3. The bioreactor or fermentor system as recited in claim 1, wherein at least portions of the first drive line and the second drive line are laterally spaced apart and disposed in parallel alignment.

4. The bioreactor or fermentor system as recited in claim 1, wherein the at least one tie comprises a first tie that connects to the first drive line and the second drive line at a plurality of spaced apart locations along the length of the first drive line and the second drive line.

5. The bioreactor or fermentor system as recited in claim 1, wherein at least 50% of the length of the first drive line and the second drive line are maintained at lateral spaced apart positions within the compartment of the container.

6. The bioreactor or fermentor system as recited in claim 1, wherein the first drive line and the second drive line both extend between the first end and the second end of the container.

7. The bioreactor or fermentor system as recited in claim 1, wherein the first drive line and the second drive line each have a longitudinal axis extending along the length thereof, at least 40% of the length of the first drive line and/or the second drive line being sufficient flexible that it can be twisted under torsion about its longitudinal axis over the angle of at least 180°, without plastic deformation.

8. The bioreactor or fermentor system as recited in claim 1, wherein the first drive line and the second drive line each have a longitudinal axis extending along the length thereof, at least 40% of the length of the first drive line and/or the second drive line being sufficiently flexible that it can be bent along the longitudinal axis at an angle of at least 90° without plastic deformation of the drive line.

9. The bioreactor or fermentor system as recited in claim 1, wherein the first drive line and/or the second drive line comprises a flexible cable, cord, tube, or solid line.

10. The bioreactor or fermentor system as recited in claim 1, wherein the first drive line and/or the second drive line comprises a plurality of polymeric strands woven together.

11. The bioreactor or fermentor system as recited in claim 1, further comprising at least one mixing element secured to the at least one tie or secured to the first drive line and/or second drive line.

12. The bioreactor or fermentor system as recited in claim 11, wherein the at least on mixing element comprises an impeller, the impeller comprising a hub and a plurality of blades outwardly projecting from the hub.

13. The bioreactor or fermentor system as recited in claim 1, wherein the container comprises a collapsible bag formed from one or more sheets of polymeric film.

14. The bioreactor or fermentor system as recited in claim 1, wherein the first drive line and the second drive line are concurrently rotatable about a common axis of rotation.

15. The bioreactor or fermentor system as recited in claim 1, further comprising means for rotating the first drive line and the second drive line within the compartment of the container.

16. The bioreactor or fermentor system as recited in claim 1, wherein the at least one tie comprises:
  a first plurality of ties that are spaced apart and extend between the first drive line and the second drive line, the first plurality of ties being free of any impeller mounted thereon; and
  a second plurality of ties that are spaced apart and extend between the first drive line and the second drive line, each of the second plurality of ties having an impeller coupled thereon, each impeller comprising a hub and a plurality of blades outwardly projecting therefrom.

17. The bioreactor or fermentor system as recited in claim 1, further comprising a port disposed on the container and a pH probe or dissolved oxygen probe being coupled with the probe.

18. The bioreactor or fermentor system as recited in claim 1, further comprising biological culture disposed with the compartment of the container, the biological culture being comprised of cells or microorganisms and a medium.

19. The bioreactor or fermentor system as recited in claim 1, wherein the first end of the first drive line and the first end of the second drive line are integrally connected together so that the first drive line and the second drive line form one continuous dive line.

20. The bioreactor or fermentor system as recited in claim 1, wherein the first end of the first drive line and the second drive line are rotatably connected to the first end of the container and the second end of the first drive line and the second drive line are rotatably connected to the second end of the container so that when the first end of the first drive line and the second drive line are rotated relative to the container, the first drive line and the second drive line each twist into a helical configuration so as to place each of the first drive line and the second drive line in tension.

* * * * *